(12) United States Patent
Frohberg

(10) Patent No.: US 6,791,010 B1
(45) Date of Patent: Sep. 14, 2004

(54) NUCLEIC ACID MOLECULE CODING FOR BETA-AMYLASE, PLANTS SYNTHESIZING A MODIFIED STARCH, METHOD OF PRODUCTION AND APPLICATIONS

(75) Inventor: Claus Frohberg, Berlin (DE)

(73) Assignee: Bayer CropScience GmbH, Frankfurt (DE)

( * ) Notice: Subject to any disclaimer, the term of this patent is extended or adjusted under 35 U.S.C. 154(b) by 0 days.

(21) Appl. No.: 09/744,852

(22) PCT Filed: Jul. 30, 1999

(86) PCT No.: PCT/EP99/05523

§ 371 (c)(1),
(2), (4) Date: May 31, 2001

(87) PCT Pub. No.: WO00/08185

PCT Pub. Date: Feb. 17, 2000

(30) Foreign Application Priority Data

Jul. 31, 1998 (DE) .......................... 198 36 099

(51) Int. Cl.[7] .................. C12N 15/29; C12N 15/56; C12N 15/63; C12N 15/82; A01H 5/00
(52) U.S. Cl. .................. 800/284; 800/298; 800/317.2; 800/320.1; 800/320.2; 800/320.3; 435/183; 435/201; 435/320.1; 435/419; 536/23.1; 536/32.2; 536/23.6
(58) Field of Search .................. 435/320.1, 410, 435/424, 429, 468, 483, 200, 201, 419; 800/278, 284, 285, 286, 295, 298, 317.7, 320.1, 320.2, 320.3; 536/23.1, 23.2, 23.6

(56) References Cited

FOREIGN PATENT DOCUMENTS

| WO | WO 92/05259 |   | 4/1992 |   |
|---|---|---|---|---|
| WO | WO 94/09144 |   | 4/1994 |   |
| WO | WO 94/28149 |   | 12/1994 |   |
| WO | WO 97/24448 | * | 7/1997 | ............ C12N/15/82 |

OTHER PUBLICATIONS

Fourgoux–Nicol et al (1999, Plant Molecular Biology 40:857–872.*
Willmitzer et al., Plant Polymeric Carbohydrates, 17/1993, pp. 33–39.*
Kossmann J. et al., Progress in Biotechnology, 10, Proc. Int. Conf. 4/23–26/95 1995, pp. 271–278.*
Yoshida N. et al., Journal of Biochemistry, 1991, vol. 110, pp. 196–201.*
Sadowski J. et al., GenBank Accession No. JQ2248.*
Abel et al., Cloning and Functional Analysis of a cDNA encoding a novel 139 kDa starch synthase from potato (*Solanum tuberosum* L.), The Plant Journal, vol. 10., No. 6, pp. 981–991, 1996.
Yoshida et al., "A Nuclear Gene Encoding β–amylase of Sweet Potato", Gene, vol. 120, pp. 255–159, 1992.
Mita et al., "Sugar–Inducible Expression of a Gene for β–amylase in Arabidopsis thaliana", Plant Physiol., vol. 107, pp. 894–904, 1995.
Bhullar, S.S., Submitted Mar. 20, 1998 to the EMBL/GenBank/DDBJ databases, Molecular Plant Physiology, Max–Planck Instituet fuer Molekulare Pflanzenphysiologie, Karl–Liebknecht Str. 25, Haus 20, 14476, Golm, Germany, Database AC AJ225087, referred to as XP–002124966.

* cited by examiner

Primary Examiner—David T. Fox
Assistant Examiner—Russell Kallis
(74) Attorney, Agent, or Firm—Frommer Lawrence & Haug LLP

(57) ABSTRACT

The present invention relates to nucleic acid molecules coding for a protein with beta-amylase activity from potato and to a method for the production of transgenic plant cells and plants synthesizing a modified starch. The invention also relates to vectors and host cells containing the nucleic acid molecules according to the invention, the plant cells and plants produced using the method according to the invention and the starch synthesized by the plant cells and plants according to the invention. The invention also relates to a method of production of said starch.

20 Claims, 1 Drawing Sheet

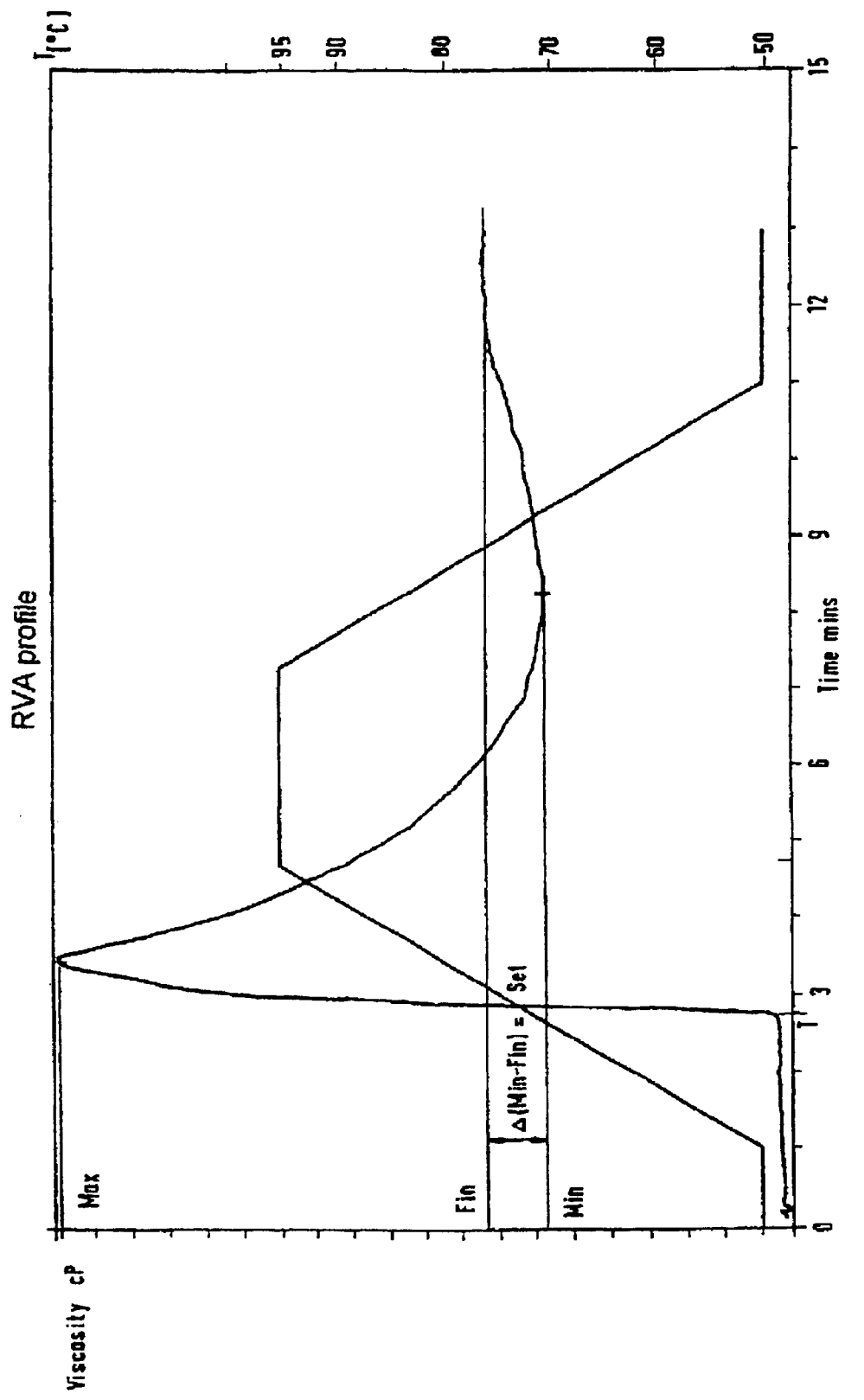

SEQUENCE LISTING

<160> NUMBER OF SEQ ID NOS: 2

<210> SEQ ID NO 1
<211> LENGTH: 1950
<212> TYPE: DNA
<213> ORGANISM: Solanum tuberosum
<220> FEATURE:
<221> NAME/KEY: CDS
<222> LOCATION: (16)..(1752)
<223> OTHER INFORMATION: coding sequence beta-amylase

<400> SEQUENCE: 1
attaatatta ttatt atg gca atg agt ctg cca cac cag atc ggt gcc tta    51

|  |  |  |  |  |  |  |  |  |  |  |  |  |  |  |  |
|---|---|---|---|---|---|---|---|---|---|---|---|---|---|---|---|
|  | Met | Ala | Met | Ser | Leu | Pro | His | Gln | Ile | Gly | Ala | Leu |  |  |  |
|  | 1 |  |  |  | 5 |  |  |  |  | 10 |  |  |  |  |  |

```
tca gga aca tcg ctc acg gcg gaa acc ggt gga gtt tca tgc gaa gtt      99
Ser Gly Thr Ser Leu Thr Ala Glu Thr Gly Gly Val Ser Cys Glu Val
         15                  20                  25 ccg gcg aag ggg agt tca gct aca tca gct atg tgg aga aca ccg atg     147
Pro Ala Lys Gly Ser Ser Ala Thr Ser Ala Met Trp Arg Thr Pro Met
 30                  35                  40 acg aat tta aaa gta tcg gta caa aaa aca gga act gaa att gac agg     195
Thr Asn Leu Lys Val Ser Val Gln Lys Thr Gly Thr Glu Ile Asp Arg
 45                  50                  55                  60 gtg tcg ccg tcg ccg tcg ccg ccg atg agt ccg atg atg gga gga gga     243
Val Ser Pro Ser Pro Ser Pro Pro Met Ser Pro Met Met Gly Gly Gly
                 65                  70                  75 atg cgg ccg gat tta tta gcg tgt caa gcg ttg atg gaa gct cag gta     291
Met Arg Pro Asp Leu Leu Ala Cys Gln Ala Leu Met Glu Ala Gln Val
             80                  85                  90 gat gag gta gtt gag aga gaa tat aag gtt agg aat tcg tcg gag aaa     339
Asp Glu Val Val Glu Arg Glu Tyr Lys Val Arg Asn Ser Ser Glu Lys
         95                 100                 105 gag aaa gga gtt ccg gtg ttt gtt atg atg ccg ttg gat agt gtg aaa     387
Glu Lys Gly Val Pro Val Phe Val Met Met Pro Leu Asp Ser Val Lys
 110                 115                 120 atg gat cat act gtg aat agg aag aag gcg atg aat gcg agt tta cag     435
Met Asp His Thr Val Asn Arg Lys Lys Ala Met Asn Ala Ser Leu Gln
125                 130                 135                 140 gcg ttg aag agc gcc ggt gtg gaa ggg att atg atg gat gtg tgg tgg     483
Ala Leu Lys Ser Ala Gly Val Glu Gly Ile Met Met Asp Val Trp Trp
                145                 150                 155 gga ttg gtg gag aga gat gcg ccg gga gag tat aat tgg ggc ggt tat     531
Gly Leu Val Glu Arg Asp Ala Pro Gly Glu Tyr Asn Trp Gly Gly Tyr
            160                 165                 170 gct gag ctt atg gaa atg gcg aaa aaa cat gga ctc aaa gtt caa gct     579
Ala Glu Leu Met Glu Met Ala Lys Lys His Gly Leu Lys Val Gln Ala
        175                 180                 185 gtg atg tct ttc cat caa tgt ggt gga aac gtc ggt gat tcc tgc acg     627
Val Met Ser Phe His Gln Cys Gly Gly Asn Val Gly Asp Ser Cys Thr
    190                 195                 200 atc cct ctt cca agg tgg gtt gtt gag gag atg gag aag gat cca gat     675
Ile Pro Leu Pro Arg Trp Val Val Glu Glu Met Glu Lys Asp Pro Asp
205                 210                 215                 220 ctt gca tac aca gat cag tgg gga agg agg aat ttt gaa tat gta tcg     723
Leu Ala Tyr Thr Asp Gln Trp Gly Arg Arg Asn Phe Glu Tyr Val Ser
                225                 230                 235 ctt ggt tgc gat aca ctt cca gtt ctt aaa gga agg act cct gtc caa     771
Leu Gly Cys Asp Thr Leu Pro Val Leu Lys Gly Arg Thr Pro Val Gln
            240                 245                 250 tgc tat tct gat ttc atg aga ggg ttt aga gat aga ttt gag aat ctc     819
Cys Tyr Ser Asp Phe Met Arg Gly Phe Arg Asp Arg Phe Glu Asn Leu
        255                 260                 265 cta ggt gac acc att gtg gaa att caa gtc ggg atg ggt cca gct gga     867
Leu Gly Asp Thr Ile Val Glu Ile Gln Val Gly Met Gly Pro Ala Gly
    270                 275                 280 gag ctc cgt tat cca tcc tat ccg gaa aaa gat gga gta tgg aaa ttc     915
Glu Leu Arg Tyr Pro Ser Tyr Pro Glu Lys Asp Gly Val Trp Lys Phe
285                 290                 295                 300 cct gga att ggt gct ttt cag tgt tat gac aag tac atg atc agt agc     963
Pro Gly Ile Gly Ala Phe Gln Cys Tyr Asp Lys Tyr Met Ile Ser Ser
                305                 310                 315
```

```
                                                                    -continued tta cag ggt gca gca gaa gct ttt ggt aag cct gaa tgg gga cac acc      1011
Leu Gln Gly Ala Ala Glu Ala Phe Gly Lys Pro Glu Trp Gly His Thr
        320                 325                 330 ggt cca acc gat gct ggt cag tac aac aat tgg cca gaa gat acc aac      1059
Gly Pro Thr Asp Ala Gly Gln Tyr Asn Asn Trp Pro Glu Asp Thr Asn
335                 340                 345 ttt ttc aag aag gaa ggt ggt gga tgg gat agt caa tat ggg gag ttc      1107
Phe Phe Lys Lys Glu Gly Gly Gly Trp Asp Ser Gln Tyr Gly Glu Phe
    350                 355                 360 ttc ctc act tgg tat tct gag atg ctt ttg aac cat ggt gag agg ata      1155
Phe Leu Thr Trp Tyr Ser Glu Met Leu Leu Asn His Gly Glu Arg Ile
365                 370                 375                 380 ctg caa tca gcc aag gcg ata ttc gag gac aag ggt gtt aag att tca      1203
Leu Gln Ser Ala Lys Ala Ile Phe Glu Asp Lys Gly Val Lys Ile Ser
                385                 390                 395 gtt aag att gca ggt att cac tgg cac tat gga aca agg tcc cat gcc      1251
Val Lys Ile Ala Gly Ile His Trp His Tyr Gly Thr Arg Ser His Ala
            400                 405                 410 cct gag ctg acc gct gga tac tac aac acc cgt aac cga gat ggt tac      1299
Pro Glu Leu Thr Ala Gly Tyr Tyr Asn Thr Arg Asn Arg Asp Gly Tyr
        415                 420                 425 ctt ccc atc gcc caa atg ctt gcc cgc cac ggt gca gtt ttc aac ttc      1347
Leu Pro Ile Ala Gln Met Leu Ala Arg His Gly Ala Val Phe Asn Phe
    430                 435                 440 aca tgt gtt gag atg cgt gac cac gag cag cca caa gat gca cta tgt      1395
Thr Cys Val Glu Met Arg Asp His Glu Gln Pro Gln Asp Ala Leu Cys
445                 450                 455                 460 gca cct gag aag ttg gtt agg caa gtg gct tta gca act cag gaa gct      1443
Ala Pro Glu Lys Leu Val Arg Gln Val Ala Leu Ala Thr Gln Glu Ala
                465                 470                 475 caa gtt cca ctt gct ggg gag aat gca ttg cca cga tac gat gat tat      1491
Gln Val Pro Leu Ala Gly Glu Asn Ala Leu Pro Arg Tyr Asp Asp Tyr
            480                 485                 490 gca cat gaa cag atc ctt caa gca tcc tca ttg aat atc aac gat caa      1539
Ala His Glu Gln Ile Leu Gln Ala Ser Ser Leu Asn Ile Asn Asp Gln
        495                 500                 505 tca ggt gat aga gag atg tgc gcg ttt aca tat ttg agg atg aat cct      1587
Ser Gly Asp Arg Glu Met Cys Ala Phe Thr Tyr Leu Arg Met Asn Pro
    510                 515                 520 gac cta ttc cat cct gat aac tgg agg cga ttc gtt gcc ttc gtg aag      1635
Asp Leu Phe His Pro Asp Asn Trp Arg Arg Phe Val Ala Phe Val Lys
525                 530                 535                 540 aaa atg aaa gaa gga aaa gac gca aac aaa tgc cgg gaa caa gta gag      1683
Lys Met Lys Glu Gly Lys Asp Ala Asn Lys Cys Arg Glu Gln Val Glu
                545                 550                 555 agg gag gca gag cat ttc gtg cat ata act cag ccg tta gtg caa gaa      1731
Arg Glu Ala Glu His Phe Val His Ile Thr Gln Pro Leu Val Gln Glu
            560                 565                 570 gct gca gct gcc ctc atg cac taagcaaatg gttgtcaaat agtactgtaa         1782
Ala Ala Ala Ala Leu Met His
        575 ttttgatcct tttagctaac atggagtttt tcaacatgtt acgaggatct tatagctcgt   1842 tatcgttctt cttatatgtt tgtaaaactg tccatcgtgt attttttcga agttagacat   1902 tatgtcttaa tgaaatgata cataattcag tagtaaaaaa aaaaaaaa                1950

<210> SEQ ID NO 2
<211> LENGTH: 579
<212> TYPE: PRT
<213> ORGANISM: Solanum tuberosum
```

<400> SEQUENCE: 2

```
Met Ala Met Ser Leu Pro His Gln Ile Gly Ala Leu Ser Gly Thr Ser
1               5                   10                  15
Leu Thr Ala Glu Thr Gly Gly Val Ser Cys Glu Val Pro Ala Lys Gly
            20                  25                  30
Ser Ser Ala Thr Ser Ala Met Trp Arg Thr Pro Met Thr Asn Leu Lys
            35                  40                  45
Val Ser Val Gln Lys Thr Gly Thr Glu Ile Asp Arg Val Ser Pro Ser
    50                  55                  60
Pro Ser Pro Pro Met Ser Pro Met Met Gly Gly Met Arg Pro Asp
65                  70                  75                  80
Leu Leu Ala Cys Gln Ala Leu Met Glu Ala Gln Val Asp Glu Val Val
                85                  90                  95
Glu Arg Glu Tyr Lys Val Arg Asn Ser Ser Glu Lys Glu Lys Gly Val
            100                 105                 110
Pro Val Phe Val Met Met Pro Leu Asp Ser Val Lys Met Asp His Thr
            115                 120                 125
Val Asn Arg Lys Lys Ala Met Asn Ala Ser Leu Gln Ala Leu Lys Ser
    130                 135                 140
Ala Gly Val Glu Gly Ile Met Met Asp Val Trp Trp Gly Leu Val Glu
145                 150                 155                 160
Arg Asp Ala Pro Gly Glu Tyr Asn Trp Gly Gly Tyr Ala Glu Leu Met
                165                 170                 175
Glu Met Ala Lys Lys His Gly Leu Lys Val Gln Ala Val Met Ser Phe
            180                 185                 190
His Gln Cys Gly Gly Asn Val Gly Asp Ser Cys Thr Ile Pro Leu Pro
            195                 200                 205
Arg Trp Val Val Glu Glu Met Glu Lys Asp Pro Asp Leu Ala Tyr Thr
    210                 215                 220
Asp Gln Trp Gly Arg Arg Asn Phe Glu Tyr Val Ser Leu Gly Cys Asp
225                 230                 235                 240
Thr Leu Pro Val Leu Lys Gly Arg Thr Pro Val Gln Cys Tyr Ser Asp
                245                 250                 255
Phe Met Arg Gly Phe Arg Asp Arg Phe Glu Asn Leu Leu Gly Asp Thr
            260                 265                 270
Ile Val Glu Ile Gln Val Gly Met Gly Pro Ala Gly Glu Leu Arg Tyr
            275                 280                 285
Pro Ser Tyr Pro Glu Lys Asp Gly Val Trp Lys Phe Pro Gly Ile Gly
    290                 295                 300
Ala Phe Gln Cys Tyr Asp Lys Tyr Met Ile Ser Ser Leu Gln Gly Ala
305                 310                 315                 320
Ala Glu Ala Phe Gly Lys Pro Glu Trp Gly His Thr Gly Pro Thr Asp
                325                 330                 335
Ala Gly Gln Tyr Asn Asn Trp Pro Glu Asp Thr Asn Phe Phe Lys Lys
            340                 345                 350
Glu Gly Gly Gly Trp Asp Ser Gln Tyr Gly Glu Phe Phe Leu Thr Trp
            355                 360                 365
Tyr Ser Glu Met Leu Leu Asn His Gly Glu Arg Ile Leu Gln Ser Ala
    370                 375                 380
Lys Ala Ile Phe Glu Asp Lys Gly Val Lys Ile Ser Val Lys Ile Ala
385                 390                 395                 400
Gly Ile His Trp His Tyr Gly Thr Arg Ser His Ala Pro Glu Leu Thr
```

-continued

```
                    405                 410                 415
Ala Gly Tyr Tyr Asn Thr Arg Asn Arg Asp Gly Tyr Leu Pro Ile Ala
            420                 425                 430

Gln Met Leu Ala Arg His Gly Ala Val Phe Asn Phe Thr Cys Val Glu
        435                 440                 445

Met Arg Asp His Glu Gln Pro Gln Asp Ala Leu Cys Ala Pro Glu Lys
    450                 455                 460

Leu Val Arg Gln Val Ala Leu Ala Thr Gln Glu Ala Gln Val Pro Leu
465                 470                 475                 480

Ala Gly Glu Asn Ala Leu Pro Arg Tyr Asp Asp Tyr Ala His Glu Gln
            485                 490                 495

Ile Leu Gln Ala Ser Ser Leu Asn Ile Asn Asp Gln Ser Gly Asp Arg
            500                 505                 510

Glu Met Cys Ala Phe Thr Tyr Leu Arg Met Asn Pro Asp Leu Phe His
        515                 520                 525

Pro Asp Asn Trp Arg Arg Phe Val Ala Phe Val Lys Lys Met Lys Glu
    530                 535                 540

Gly Lys Asp Ala Asn Lys Cys Arg Glu Gln Val Glu Arg Glu Ala Glu
545                 550                 555                 560

His Phe Val His Ile Thr Gln Pro Leu Val Gln Glu Ala Ala Ala Ala
            565                 570                 575

Leu Met His
```

NUCLEIC ACID MOLECULE CODING FOR BETA-AMYLASE, PLANTS SYNTHESIZING A MODIFIED STARCH, METHOD OF PRODUCTION AND APPLICATIONS

The present invention relates to nucleic acid molecules which encode a protein with the activity of a potato β-amylase, and to processes for the generation of transgenic plant cells and plants which synthesize a modified starch. Moreover, the present invention relates to vectors and host cells comprising the nucleic acid molecules according to the invention, to the plant cells and plants originating from the processes according to the invention, to the starch synthesized by the plant cells and plants according to the invention, and to processes for the production of this starch.

Taking into consideration the increasing importance attached to plant constituents as renewable raw materials, biotechnology research attempts to adapt plant-based raw materials to the needs of the processing industry. To allow renewable raw materials to be used in as many fields of application as possible, it is therefore necessary to provide a multiplicity of substances.

Besides oils, fats and proteins, polysaccharides constitute important renewable raw materials from plants. Besides cellulose, starch, which is one of the most important storage substances in higher plants, occupies a central position amongst the polysaccharides. Besides maize, rice and wheat, potatoes play an important role, in particular in starch production.

The polysaccharide starch is a polymer of chemically uniform units, the glucose molecules. However, it is a highly complex mixture of different forms of molecules which differ with regard to their degree of polymerization and the occurrence of branchings of the glucose chains. Starch therefore constitutes no uniform raw material. In particular, we differentiate between amylose starch, an essentially unbranched polymer of α-1,4-glycosidically linked glucose molecules, and amylopectin starch, which, in turn, constitutes a complex mixture of differently branched glucose chains. The branchings are generated by the occurrence of additional α-1,6-glycosidic linkages. In typical plants used for starch production such as, for example, maize or potatoes, the starch synthesized consists of approx. 25% amylose starch and approx. 75% amylopectin starch.

The molecular structure of starch, which is determined to a great extent by the degree of branching, the amylose/amylopectin ratio, the average length and distribution of the side chains, and the presence of phosphate groups, is decisive for important functional properties of starch or its aqueous solutions. Examples of functional properties which must be mentioned in this context are solubility, the retrogradation behavior, the film-forming properties, the viscosity, the color stability, the gelatinization properties, and binding and adhesive properties. The starch granule size may also be of importance for various uses. Also, the generation of high-amylose starches is of particular interest for certain applications. Furthermore, a modified starch present in plant cells can advantageously modify the behavior of the plant cell under certain conditions. For example, it is feasible to reduce starch breakdown during the storage of starch-containing organs, such as, for example, seeds or tubers, prior to their further processing, for example for extracting the starch. It is furthermore of interest to prepared modified starches which lead to plant cells or plant organs containing this starch being better suited to processing, for example in the production of foods such as popcorn or cornflakes from maize, or the production of French fries, chips or potato powder from potatoes. Of particular interest in this context is an improvement of the starches with regard to reduced cold sweetening, i.e. a reduced liberation of reducing sugars (in particular glucose) upon prolonged storage at low temperatures. Potatoes especially are frequently stored at temperatures from 4 to 8° C. in order to minimize starch breakdown during storage. The reducing sugars liberated during this process, in particular glucose, result in undesired browning reactions (so-called Maillard reactions) in the production of French fries or crisps.

The starch which can be isolated from plants is frequently adapted to particular industrial purposes with the aid of chemical modifications which, as a rule, require time and money. It seems therefore desirable to find possibilities of generating plants which synthesize starch whose properties already meet the specific demands of the processing industry and thus combine economical and ecological advantages.

One possibility of providing such plants is, in addition to plant breeding measures, the directed genetic modification of the starch metabolism of starch-producing plants by recombinant methods. However, a prerequisite therefor is the identification and characterization of the enzymes which participate in starch synthesis modification and starch breakdown (starch metabolism) and the isolation of the corresponding DNA sequences which encode these enzymes.

The biochemical synthetic pathways which lead to the synthesis of starch are essentially known. In plant cells, starch synthesis takes place in the plastids. In photosynthetically active tissues, these plastids are the chloroplasts, in photosynthetically inactive, starch-storing tissue the amyloplasts.

Important enzymes which are involved in starch metabolism are, for example, the branching enzymes, ADP glucose pyrophosphorylases, granule-bound starch synthases, soluble starch synthases, debranching enzymes, disproportioning enzymes, plastid starch phosphorylases, the R1 enzymes (R1 proteins), amylases or glucosidases.

It is an object of the present invention to provide other, or alternative, recombinant approaches for modifying the starch metabolism in starch-synthesizing plants (for example rye, barley, oats, maize, wheat, sorghum and millet, sago, rice, peas, marrowfat peas, cassava, potatoes, tomatoes, oilseed rape, soybeans, hemp, flax, sunflowers, cowpeas, mung beans, beans, bananas or arrowroot) suitable nucleic acid molecules by means of which plant cells can be transformed, thus allowing the synthesis of modified, advantageous starch species.

Such modified starch species exhibit, for example, modifications regarding their degree of branching, the amylose/amylopectin ratio, the phosphate content, the starch granule size and/or the average length and distribution of the side chains (i.e. side chain structure).

It is a further object of the invention to provide methods which allow the generation of transgenic plants which synthesize a modified starch species.

Surprisingly, transgenic plants which have been transformed with the nucleic acid molecules according to the invention synthesize a starch whose physicochemical properties and/or whose side chain structure is modified in the particular manner so that the abovementioned objects are achieved by providing the use forms specified in the claims.

The invention therefore relates to a nucleic acid molecule encoding a protein with the function of a potato β-amylase, selected from the group consisting of a) nucleic acid molecules which encode a protein which encompasses the amino acid sequence stated under SEQ ID NO: 2 or its derivatives or parts, b) nucleic acid molecules which encompass the nucleotide sequence shown under SEQ ID NO: 1 or its derivatives or parts, or a corresponding ribonucleotide sequence;

c) nucleic acid molecules which hybridize with, or are complementary to, preferably which hybridize specifically with, the nucleic acid molecules stated under a) or b), and d) nucleic acid molecules whose nucleotide sequence deviates from the sequence of the nucleic acid molecules stated under a), b) or c) owing to the degeneracy of the genetic code.

Accordingly, the present invention relates to a nucleic acid molecule which encodes a β-amylase and which comprises an amino acid sequence of SEQ ID NO: 2 or its derivatives or parts in accordance with the cDNA insert of the plasmid St-b-Amy (DSM No. 12348). The abovementioned β-amylase to, according to the invention is involved in the starch metabolism of potatoes and is directly or indirectly involved in starch biosynthesis.

The term "derivative" with regard to the β-amylase protein (or its polypeptide, amino acid sequence) of the invention encompasses, for the purposes of the present invention, a polypeptide which is derived from SEQ ID NO: 1 and which comprises at least 86 amino acid residues, preferably at least 120, in particular at least 155 and very especially preferably approximately 163–170 amino acid residues which are selected from the group of the amino acid residues consisting of 112 V, 113 P, 114 V, 116 V, 117 M, 119 P, 120 L, 139 L, 142 L, 145 A, 146 G, 147 V, 149 G, 151 M, 153 D, 155 W, 156 W, 157 G, 160 E, 164 P, 167 Y, 169 W, 172 Y, 175 L, 183 G, 184 L, 185 K, 187 Q, 190 M, 191 S, 192 F, 193 H, 195 C, 196 G, 197 G, 198 N, 199 V, 200 G, 201 D, 205 I, 206 P, 208 P, 210 W, 211 V, 219 P, 220 D, 223 Y, 224 T, 228 G, 230 R, 231 N, 233 E, 234 Y, 238 G, 240 D, 243 P, 247 G, 248 R, 249 T, 254 Y, 256 D, 258 M, 261 F, 262 R, 273 I, 276 I, 278 V, 279 G, 281 G, 282 P, 284 G, 285 E, 286 L, 287 R, 288 Y, 289 P, 290 S, 291 Y, 292 P, 298 W, 300 F, 301 P, 302 G, 303 I, 304 G, 306 F, 307 Q, 308 C, 309 Y, 310 D, 311 K, 312 Y, 321 A, 325 G, 329 W, 336 D, 337 A, 338 G, 340 Y, 344 P, 347 T, 349 F, 350 F, 362 G, 364 F, 365 F, 368 W, 369 Y, 370 S, 373 L, 376 H, 380 I, 381 L, 384 A, 388 F, 393 V, 394 K, 398 K, 401 G, 402 I, 403 H, 404 W, 406 Y, 411 H, 412 A, 414 E, 415 L, 416 T, 417 A, 418 G, 419 Y, 420 Y, 421 N, 426 D, 427 G, 428 Y, 430 P, 431 I, 432 A, 438 H, 443 N, 444 F, 445 T, 446 C, 448 E, 449 M, 453 E, 454 Q, 458 A, 462 P, 465 L, 466 V, 468 Q, 469 V, 481 A, 483 E, 484 N, 485 A, 486 L, 488 R, 489 Y, 490 D, 493 A, 496 Q, 518 T, 519 Y, 520 L, 521 R, 526 L, 538 F, 539 V and 542 M of SEQ ID NO: 2 and which comprises at least approximately 1–61, preferably at least 122, in particular at least 170, more preferably at least 220 and very especially preferably approximately 232–241 amino acid residues which are selected from the group of the amino acid residues consisting of 1 M, 2 A, 3 M, 4 S, 5 L, 6 P, 7 H, 8 Q, 9 I, 10 G, 11 A, 12 L, 13 S, 14 G, 15 T, 16 S, 17 L, 18 T, 19 A, 20 E, 21 T, 22 G, 23 G, 24 V, 25 S, 26 C, 27 E, 28 V, 29 P, 30 A, 31 K, 32 G, 33 S, 34 S, 35 A, 36 T, 38 A, 39 M, 40 W, 41 R, 42 T, 44 M, 45 T, 46 N, 47 L, 48 K, 49 V, 50 S, 51 V, 52 Q, 53 K, 54 T, 55 G, 56 T, 57 E, 58 I, 59 D, 60 R, 61 V, 62 S, 63 P, 64 S, 65 P, 66 S, 67 P, 68 P, 69 M, 70 S, 71 P, 73 M, 74 G, 75 G, 76 G, 78 R, 79 P, 80 D, 81 L, 82 L, 84 C, 85 Q, 86 A, 87 L, 88 M, 89 E, 90 A, 91 Q, 92 V, 93 D, 94 E, 95 V, 96 V, 97 E, 98 R, 99 E, 100 Y, 101 K, 103 R, 105 S, 107 E, 108 K, 109 E, 110 K, 111 G, 118 M, 122 S, 124 K, 126 D, 127 H, 128 T, 131 R, 132 K, 133 K, 140 Q, 144 S, 152 M, 161 R, 163 A, 170 G, 176 M, 177 E, 180 K, 186 V, 204 T, 209 R, 212 V, 215 M, 222 A, 226 Q, 227 W, 232 F, 235 V, 241 T, 242 L, 246 K, 251 V, 253 C, 260 G, 263 D, 267 N, 271 D, 272 T, 294 K, 295 D, 297 V, 299 K, 305 A, 314 I, 319 G, 323 A, 324 F, 331 H, 332 T, 335 T, 339 Q, 343 W, 348 N, 352 K, 353 E, 355 G, 356 G, 358 D, 360 Q, 363 E, 371 E, 372 M, 378 E, 382 Q, 383 S, 385 K, 386 A, 387 I, 389 E, 390 D, 391 K, 392 G, 395 I, 397 V, 399 I, 407 G, 413 P, 433 Q, 442 F, 447 V, 452 H, 456 Q, 459 L, 467 B, 470 A, 471 L, 474 Q, 475 E, 477 Q, 478 V, 479 P, 491 D, 492 Y, 494 H, 495 E, 499 Q, 500 A, 501 S, 502 S, 503 L, 505 I, 506 N, 508 Q, 509 S, 511 D, 513 E, 515 C, 524 P, 528 H, 529 P, 530 D, 534 R, 537 A, 546 K, 548 A, 549 N, 550 K, 551 C, 552 R, 555 V, 556 E, 558 E, 559 A, 560 E, 561 H, 562 F, 564 H, 565 I, 566 T, 567 Q, 568 P, 569 L, 570 V, 571 Q, 573 A, 574 A, 575 A, 576 A, 577 L, 578 M and 579 H (here identified by the single-letter code for amino acids) of SEQ ID NO: 2.

The term "part" with regard to the β-amylase protein (polypeptide, amino acid sequence) according to the invention encompasses, for the purposes of the present invention, a poly- or oligopeptide composed of at least approximately 10–19, preferably at least 80, more preferably at least 160, especially preferably at least 320 and most preferably approximately 400–550 of the amino acid residues of the β-amylase encoded by the nucleic acid molecule according to the invention or its derivatives.

The present invention furthermore relates to a nucleic acid molecule which comprises a nucleic acid molecule of SEQ ID NO: 1 in accordance with the cDNA insert of the plasmid DSM No. 12348 deposited at the DSZM on Jul. 24, 1998, or its derivatives or parts, in particular of the coding region or its derivatives or parts.

The term "derivative" with regard to the nucleic acid molecule (nucleotide sequence or polynucleotide) according to the invention encompasses, for the purposes of this invention, a polynucleotide which comprises at least 246 nucleotides, preferably at least 344, in particular at least 443, and very especially preferably approximately 467–487 nucleotides selected from the group consisting of 241 T, 245 T, 257 C, 268 G, 272 A, 279 T, 285 A, 290 A, 291 G, 307 A, 309 G, 311 A, 314 C, 320 A, 322 A, 323 A, 325 G, 334 G, 335 T, 337 C, 338 C, 340 G, 341 T, 343 T, 346 G, 347 T, 349 A, 350 T, 351 G, 353 T, 355 C, 356 C, 359 T, 361 G, 368 T, 370 A, 386 T, 400 G, 404 T, 406 A, 409 G, 416 T, 420 G, 425 T, 433 G, 434 C, 436 G, 437 G, 439 G, 440 T, 442 G, 443 A, 445 G, 446 G, 449 T, 451 A, 452 T, 453 G, 457 G, 458 A, 460 G, 463 T, 464 G, 465 G, 466 T, 467 G, 468 G, 469 G, 470 G, 473 T, 476 T, 478 G, 479 A, 487 G, 490 C, 491 C, 499 T, 500 A, 503 A, 505 T, 506 G, 507 G, 511 G, 514 T, 515 A, 524 T, 527 T, 533 T, 535 G, 539 A, 542 A, 547 G, 548 G, 551 T, 553 A, 554 A, 557 T, 559 C, 560 A, 562 G, 566 T, 568 A, 569 T, 570 G, 571 T, 572 C, 574 T, 575 T, 576 C, 577 C, 578 A, 583 T, 584 G, 586 G, 587 G, 589 G, 590 G, 592 A, 593 A, 595 G, 596 T, 598 G, 599 G, 601 G, 602 A, 610 A, 613 A, 614 T, 615 C, 616 C, 617 C, 620 T, 622 C, 623 C, 628 I, 629 G, 630 G, 631 G, 632 T, 637 G, 638 A, 653 A, 655 C, 656 C, 658 G, 659 A, 662 T, 667 T, 668 A, 669 C, 670 A, 671 C, 682 G, 683 G, 689 G, 690 G, 691 A, 692 A, 697 G, 698 A, 700 T, 701 A, 704 T, 710 T, 712 G, 713

G, 718 G, 719 A, 727 C, 728 C, 731 T, 734 T, 739 G, 740 G, 742 A, 743 G, 745 A, 746 C, 749 C, 752 T, 755 A, 760 T, 761 A, 766 G, 767 A, 768 T, 769 T, 771 C, 772 A, 773 T, 774 G, 779 G, 781 T, 782 T, 785 G, 787 G, 788 A, 794 T, 806 T, 811 G, 817 A, 818 T, 823 G, 824 A, 826 A, 827 T, 830 A, 832 G, 833 T, 835 G, 836 G, 839 T, 841 G, 842 G, 844 C, 845 C, 850 G, 851 G, 853 G, 854 A, 857 T, 860 G, 862 T, 863 A, 865 C, 866 C, 868 T, 869 C, 871 T, 872 A, 874 C, 875 C, 878 A, 880 A, 884 A, 886 G, 887 G, 892 T, 893 G, 894 G, 898 T, 899 T, 901 C, 902 C, 904 G, 905 G, 907 A, 908 T, 910 G, 911 G, 916 T, 917 T, 919 C, 920 A, 922 T, 923 G, 925 T, 926 A, 928 G, 929 A, 930 C, 931 A, 932 A, 934 T, 935 A, 938 T, 949 T, 950 T, 961 G, 962 C, 973 G, 974 G, 977 A, 980 C, 983 A, 985 T, 986 G, 987 G, 988 G, 1000 C, 1001 C, 1006 G, 1007 A, 1009 G, 1010 C, 1012 G, 1013 G, 1018 T, 1019 A, 1020 C, 1021 A, 1022 A, 1025 A, 1030 C, 1031 C, 1033 G, 1034 A, 1039 A, 1040 C, 1045 T, 1046 T, 1048 T, 1049 T, 1050 C, 1051 A, 1060 G, 1069 T, 1075 A, 1079 A, 1082 A, 1084 G, 1085 G, 1090 T, 1091 T, 1093 T, 1094 T, 1095 C, 1097 T, 1102 T, 1103 G, 1104 G, 1105 T, 1106 A, 1108 T, 1109 C, 1118 T, 1121 T, 1124 A, 1126 C, 1127 A, 1130 G, 1139 T, 1187 C, 1192 A, 1193 A, 1196 T, 1199 C, 1201 G, 1202 G, 1204 A, 1205 T, 1207 C, 1208 A, 1209 C, 1210 T, 1211 G, 1212 G, 1216 T, 1217 A, 1227 G, 1231 C, 1232 A, 1234 G, 1235 C, 1238 C, 1240 G, 1241 A, 1243 C, 1244 T, 1246 A, 1247 C, 1249 G, 1250 C, 1252 G, 1253 G, 1255 T, 1256 A, 1258 T, 1259 A, 1260 C, 1261 A, 1262 A, 1263 C, 1276 G, 1277 A, 1279 G, 1280 G, 1282 T, 1283 A, 1285 C, 1288 C, 1289 C, 1291 A, 1292 T, 1294 G, 1295 C, 1300 A, 1301 T, 1304 T, 1312 C, 1313 A, 1318 G, 1322 T, 1325 T, 1327 A, 1328 A, 1330 T, 1331 T, 1333 A, 1334 C, 1336 T, 1337 G, 1342 G, 1343 A, 1344 G, 1345 A, 1346 T, 1347 G, 1352 A, 1353 C, 1357 G, 1358 A, 1360 C, 1361 A, 1370 A, 1372 G, 1373 C, 1379 G, 1382 C, 1384 C, 1385 C, 1388 A, 1394 T, 1396 G, 1397 T, 1401 G, 1402 C, 1403 A, 1405 G, 1406 T, 1414 G, 1422 G, 1426 G, 1439 T, 1441 G, 1442 C, 1445 G, 1447 G, 1448 A, 1450 A, 1451 A, 1453 G, 1454 C, 1457 T, 1463 G, 1465 T, 1465 A, 1468 G, 1469 A, 1477 G, 1478 C, 1481 A, 1490 T, 1511 A, 1520 A, 1541 T, 1546 G, 1550 T, 1552 A, 1553 C, 1555 T, 1556 A, 1559 T, 1562 G, 1565 T, 1577 T, 1580 T, 1591 A, 1592 A, 1594 T, 1603 T, 1604 T, 1612 T, 1613 T, 1615 G, 1616 T, 1621 A, 1622 A, 1624 A, 1625 T, 1626 G, 1628 A, 1630 G, 1633 G, 1640 A, 1661 A, 1683 T, 1692 T, 1713 A, 1719 T, 1728 C and 1731 C of SEQ ID NO: 1 and which furthermore comprises at least approximately 1–127 nucleotides, preferably at least 253, in particular at least 354, more preferably at least 455 and very especially preferably approximately 481–501 nucleotides selected from the group consisting of 1 A, 2 T, 3 G, 4 G, 5 C, 6 A, 7 A, 8 T, 9 G, 10 A, 11 G, 12 T, 13 C, 14 T, 15 G, 16 C, 17 C, 18 A, 19 C, 20 A, 21 C, 22 C, 23 A, 24 G, 25 A, 26 T, 27 C, 28 G, 29 G, 30 T, 31 G, 32 C, 33 C, 34 T, 35 T, 36 A, 37 T, 38 C, 39 A, 40 G, 41 G, 42 A, 43 A, 44 C, 45 A, 46 T, 47 C, 48 G, 49 C, 50 T, 51 C, 52 A, 53 C, 54 G, 55 G, 56 C, 57 G, 58 G, 59 A, 60 A, 61 A, 62 C, 63 C, 64 G, 65 G, 66 T, 67 G, 68 G, 69 A, 70 G, 71 T, 72 T, 73 T, 74 C, 75 A, 76 T, 77 G, 78 C, 79 G, 80 A, 81 A, 82 G, 83 T, 84 T, 85 C, 86 A, 87 G, 88 G, 89 C, 90 G, 92 A, 93 G, 94 A, 95 G, 96 G, 97 A, 99 T, 102 A, 103 G, 104 C, 105 T, 106 A, 109 T, 110 C, 111 A, 112 G, 113 C, 115 A, 116 T, 117 G, 118 T, 120 G, 121 A, 122 G, 123 A, 124 A, 125 C, 126 A, 127 C, 129 G, 131 T, 132 G, 133 A, 134 C, 135 G, 137 A, 138 T, 139 T, 140 T, 141 A, 142 A, 143 A, 144 A, 146 T, 148 T, 149 C, 150 G, 152 T, 153 A, 154 C, 155 A, 157 A, 160 A, 161 C, 162 A, 163 G, 165 A, 166 A, 167 C, 169 G, 171 A, 172 A, 174 T, 175 G, 176 A, 178 A, 179 G, 180 G, 181 G, 183 G, 184 T, 185 C, 188 C, 189 G, 190 T, 191 C, 195 G, 196 T, 199 C, 200 C, 201 G, 202 C, 203 C, 204 G, 205 A, 206 T, 207 G, 208 A, 209 G, 210 T, 211 C, 216 G, 217 A, 213 T, 226 G, 228 A, 229 A, 231 G, 233 G, 234 G, 237 G, 238 G, 239 A, 244 T, 246 A, 247 G, 250 T, 252 T, 254 A, 256 G, 260 T, 262 A, 263 T, 274 G, 275 T, 276 A, 277 G, 278 A, 284 T, 286 G, 287 T, 288 T, 293 G, 295 G, 297 A, 298 T, 301 A, 302 A, 304 G, 306 T, 308 G, 310 A, 313 T, 315 G, 324 A, 327 G, 328 A, 331 G, 333 A, 348 T, 352 A, 354 G, 358 T, 360 G, 363 T, 365 G, 369 G, 379 C, 383 C, 392 G, 393 G, 394 A, 395 A, 396 G, 397 A, 402 G, 408 T, 417 A, 419 A, 424 T, 430 A, 432 C, 447 G, 488 C, 495 A, 519 T, 528 G, 529 G, 538 A, 549 A, 556 G, 558 T, 567 G, 573 T, 588 T, 600 T, 611 C, 612 G, 618 T, 619 C, 621 T, 626 G, 633 T, 634 G, 639 G, 645 G, 657 A, 665 C, 666 A, 678 G, 681 G, 684 A, 687 G, 693 T, 694 T, 695 T, 703 G, 705 A, 708 G, 709 C, 717 C, 723 A, 726 T, 729 A, 732 T, 744 G, 747 T, 751 G, 756 A, 757 T, 758 G, 762 T, 777 A, 778 G, 780 G, 783 T, 789 T, 799 A, 805 C, 814 A, 815 C, 816 C, 859 C, 861 T, 854 T, 879 A, 882 A, 883 G, 885 T, 889 G, 890 T, 891 A, 912 T, 914 C, 915 T, 941 T, 942 C, 943 A, 951 A, 952 C, 956 C, 966 A, 970 T, 978 G, 992 A, 995 C, 996 C, 999 T, 1003 A, 1004 C, 1014 T, 1015 C, 1026 T, 1027 T, 1028 G, 1029 G, 1042 A, 1055 A, 1062 T, 1065 T, 1066 G, 1067 G, 1072 G, 1078 C, 1080 A, 1087 G, 1098 C, 1115 T, 1119 T, 1120 T, 1134 G, 1144 C, 1146 A, 1147 T, 1148 C, 1155 G, 1156 G, 1157 C, 1159 A, 1161 A, 1165 G, 1166 A, 1169 A, 1171 A, 1172 A, 1173 G, 1174 G, 1175 G, 1179 T, 1183 A, 1186 T, 1191 T, 1195 A, 1197 T, 1200 A, 1203 T, 1219 G, 1224 A, 1233 T, 1237 C, 1245 G, 1267 C, 1281 T, 1296 C, 1305 T, 1311 C, 1320 A, 1350 T, 1354 C, 1355 A, 1356 C, 1365 A, 1366 C, 1368 A, 1377 A, 1386 T, 1393 T, 1400 G, 1408 G, 1409 C, 1410 T, 1411 T, 1412 T, 1413 A, 1420 C, 1421 A, 1423 G, 1428 T, 1429 C, 1432 G, 1435 C, 1436 C, 1456 T, 1472 A, 1474 T, 1476 T, 1479 A, 1483 G, 1485 A, 1494 T, 1499 C, 1500 A, 1501 T, 1503 C, 1504 T, 1507 T, 1508 T, 1509 G, 1514 T, 1516 A, 1517 A, 1525 T, 1526 C, 1527 A, 1528 G, 1529 G, 1533 T, 1536 A, 1538 A, 1544 G, 1557 T, 1558 T, 1560 G, 1569 T, 1570 C, 1571 C, 1575 C, 1581 C, 1582 C, 1584 T, 1585 C, 1588 G, 1590 T, 1593 C, 1597 A, 1601 G, 1608 T, 1629 A, 1635 A, 1636 A, 1638 A, 1641 C, 1643 C, 1644 A, 1646 A, 1647 C, 1649 A, 1651 T, 1652 G, 1655 G, 1664 T, 1666 G, 1668 G, 1674 G, 1676 C, 1678 G, 1680 G, 1682 A, 1686 C, 1687 G, 1690 C, 1693 A, 1696 A, 1698 T, 1708 G, 1712 A, 1724 C, 1725 T, 1727 C, 1729 C, 1730 T, 1732 A, 1734 G, 1735 C, 1736 A and 1738 T of SEQ ID NO: 1.

In the numbering of the positions of the individual elements of the nucleotide or amino acid sequences according to the invention of SEQ ID NO: 1 or SEQ ID NO: 2, which has been stated above explicitly, derivatives of said sequences according to the invention are also to be understood as meaning those sequences in which the numbering of the individual sequence elements may deviate from those of the SEQ ID NO: 1 or 2 according to the invention. What is decisive here is significant agreement of at least one sequence section ("part") with the sequence according to the invention. Such agreements can be determined in a simple manner using general expert knowledge, for example by making use of suitable computer programs, for example by carrying out a sequence comparison of the sequence according to the invention with a sequence in question to be compared (so-called sequence alignment). Such computer programs, which, for example, are commercially available (for example Omiga®, Version 1.1.3, by Oxford Molecular Ltd., Oxford, UK) and which in some cases are also an integral component of sequence databases (for example EMBL, GenBank), identify, for example, the best-possible agreement of identical, or, if appropriate, chemical equivalent, sequence elements and take into consideration in particular the existence of insertions and/or deletions which may lead to a shift of individual sequence elements or of sequence sections and which can thus affect numbering of the sequence elements or sequence sections.

With regard to the nucleic acid molecule according to the invention which encodes a β-amylase, the term "derivative" furthermore encompasses a nucleic molecule which deviates from SEQ ID NO: 1 by addition, deletion, insertion or recombination of one or more nucleotides and which meets the conditions as defined above.

With regard to the nucleic acid molecule according to the invention which encodes a β-amylase, the term "derivative" furthermore comprises a complementary or inverted-complementary sequence (polynucleotide) of the nucleic acid molecule according to the invention or of derivatives or parts thereof.

The term "part", which refers to the nucleic acid molecule according to the present invention which encodes a β-amylase, encompasses a poly- or oligonucleotide composed of at least approximately 15–35, preferably at least approximately 36–100, in particular at least 200, more preferably at last 400, especially preferably at least 800 and most preferably approximately 1400–1700 of the nucleotides of a nucleic acid molecule according to the invention which encodes a β-amylase, or their derivatives.

In a preferred embodiment of the present invention, the terms "derivative" and/or "part" according to the present invention encompass a polynucleotide, or a poly- or oligopeptide as defined above, which shows functional and/or structural equivalence of the β-amylase gene obtained from potato (i.e. of the nucleic acid molecule which encodes the β-amylase) or β-amylase polypeptide. The term "functional and/or structural equivalence" generally means the same, an equivalent or similar function of the inventive molecule in question, if appropriate especially biological function.

The invention furthermore relates to a recombinant nucleic acid molecule comprising a) a nucleotide sequence encoding a protein with the function of a β-amylase, preferably from potato, or parts of said nucleotide sequence, and b) one or more nucleotide sequences which encode a protein selected from amongst group A, composed of proteins with the function of branching enzymes, ADP glucose pyrophosphorylases, granule-bound starch synthases, soluble starch synthases, debranching enzymes, disproportioning enzymes, plastid starch phosphorylases, R1 enzymes, amylases, glucosidases, parts of nucleotide sequences encoding proteins selected from amongst group A and nucleic acid molecules which hybridize with one of said nucleotide sequences or parts thereof, preferably a deoxyribonucleic acid or ribonucleic acid molecule, especially preferably a cDNA molecule. Especially preferred is a nucleic acid molecule which specifically hybridizes with one of said nucleotide sequences or parts thereof.

The nucleotide sequence according to the invention encoding a protein with the function of a potato β-amylase is depicted by Seq ID No. 1, the protein encoded by the nucleotide sequence by Seq ID No. 2.

SEQ ID NO: 1
attaatattattattatggcaatgagtctgccacaccagatcggtgccttatcaggaacatcgctcacggcgg aaaccggtggagtttcatgcgaagttccggcgaaggggagttcagctacatcagctatgtggagaacaccgatgacgaatttaaaagtatcggtacaaaaaacaggaactgaaattgacagggtgtcgccgtcgccgtc gccgccgatgagtccgatgatgggaggaggaatgcggccggatttattagcgtgtcaagcgttg atggaagctcaggtagatgaggtagttgagagagaatataaggttaggaattcgtcggagaaagagaaaggagtt ccggtgtttgttatgatgccgttggatagtgtgaaaatggatcatactgtgaataggaagaaggc gatgaatgcgagtttacaggcgttgaagagcgccggtgtggaagggattatgatggatgtgtggtggggattggt ggagagagatgcgccgggagagtataattggggcggttatgctgagcttatggaaatggcgaaaa aacatggactcaaagttcaagctgtgatgtcttccatcaatgtggtggaaacgtcggtgattcctgcacgatccc tcttccaaggtggggttgttgaggagatggagaaggatccagatcttgcatacacagatcagtg gggaaggaggaatttgaatatgtatcgcttggttgcgatacacttcagttcttaaaggaaggactcctgtccaat gctattctgagtttcatgagagggtttagagatagatttgagaatctcctaggtgacaccatt gtggaattcaagtcgggatgggtccagctggagagctccgttatccatcctatccggaaaaagatggagtatggaaa ttccctggaattggtgcttttcagtgttatgacaagtacatgatcagtagcttacagggtgc agcagaagcttttggtaagcctgaatggggacacaccggtccaaccgatgctggtcagtacaacaattggccagaag ataccaacttttcaagaaggaaggtggtggatgggatagtcaatatggggagttcttcctca cttggtattctgagatgcttttgaaccatggtgagaggatactgcaatcagccaaggcgatattcgaggacaaggg gttaagatttcagttaagattgcaggattcactggcactatggaacaaggtcccatgccccctg agctgaccgctggatactacaacacccgtaaccgagatggttaccttcccatcgcccaaatgcttgcccgccacggt gcagttttcaacttcacatgtgttgagatgcgtgaccacgagcagccacaagatgcactatgt gcacctgagaagttggttaggcaagtggctttagcaactcaggaagctcaagttccacttgctggggagaatgcatt gccacgatacgatgattatgcacatgaacagatccttcaagcatcctcattgaatatcaacga tcaatcaggtgatagagagatgtgcgcgtttacatatttgaggatgaatcctgacctattccatcctgataactgg aggcgattcgttgccttcgtgaagaaaatgaaagaaggaaaagacgcaaacaaatgccgggaac aagtagagagggaggcagagcatttcgtgcatataactcagccgttagtgcaagaagctgcagct gccctcatgcactaagcaaatggttgtcaaatagtactgtaatttgatcctttagctaacatggagttttca acatgttacgaggatcttatagctcgttatcgttcttcttatatgtttgtaaaactgtccatcgtgtattttcg aagttagacattatgtcttaatgaaatgatacataattcagtagtaaaaaaaaaaaaa SEQ ID NO: 2
MAMSLPHQIGALSGTSLTAETGGVSCEV-PAKGSSATSAMWRTPMTNLKVSVQKT-GTEIDRVSPSPSPPMSP MMGGGMRPDLLACQ-ALMEAQVDEVVEREYKVRNSSEKEKGVPVFV-MMPLDSVKMDHTVNRKKAMN ASLQALK-SAGVEGIMMDVWWGLVERDAPGEYNWG-GYAELMEMAKKHGLKVQAVMSFHQCGGN-VGDSCTIPLPRW VVEEMEKDPDLAYTDQWG-RRNFEYVSLGCDTLPVLKGRTPVQCYSD-FMRGFRDRFENLLGDTIVEI QVGMGPAGEL-RYPSYPEKDGVWKFPGIGAFQCYDKYMISSLQG-AAEAFGKPEWGHTGPTDAGQYNNWPEDTNFF KKEGGGWDSQYGEFFLTWYSEMLLNHGERILQ-SAKAIFEDKGVKISVKIAGIWHYGTRSHA-PELTA GYYNTRNRDGYLPIAQMLRHGAVFN-FTCVEMRDHEQPQDALCAPEKLVRQV-ALATQEAQVPLAGENALPRYDD YAHEQILQ-ASSLNINDQSGDREMCAFTYLRMNPDLF-HPDNWRRFVAFVKKMKEGKDANKCREQVERE AEHFVHITQPLVQEAAAALMH The β-amylase nucleotide sequence according to the invention shows relatively little sequence homology with known β-amylase-encoding molecules (Wang et al., 1997, Plant Physiol. 113(2):403409; Yoshigi et al., 1994, Biotechn. & Biochem. 58(6):1080–1086; Monroe et al.; 1991, Plant Physiol. 97:1599–1601). The amino acid sequence differs, moreover, from the β-amylases described in the prior art by an additional N-terminal sequence (amino acids of position 1–25), which is also represented corresponding to the plane of the nucleotide sequence.

Nucleotide sequences which encode a protein of group A and which are suitable according to the invention have been described, for example, for soluble (types I, II, III or IV) or granule-bound starch synthase isoforms in Hergersberg, 1988, Ph.D. thesis, University of Cologne; Abel, 1995, Ph.D. thesis, FU Berlin; Abel et al., 1996, Plant Journal 10(6):981–991; Visser et al., 1989, Plant Sci. 64:185–192; van der Leij et al., 1991, Mol. Gen. Genet. 228:240–248; EP-A-0779363; WO 92/11376; WO 96/15248; WO 97/26362; WO 97/44472; WO 97/45545; Delrue et al., 1992, J. Bacteriol. 174: 3612–3620; Baba et al., 1993, Plant Physiol. 103:565–573; Dry et al., 1992, The Plant Journal 2,2: 193–202 or else in the EMBL database entries X74160; X58453; X88789; X 94400; for branching enzyme isoforms (branching enzymes I, IIa or IIb), debranching enzyme isoforms (debranching enzyme, isoamylases, pullulanases, R1 enzymes) or disproportioning enzyme isoforms, for example, described in WO 92/14827; WO 95/07335; WO 95/09922; WO 96/19581; WO 97/22703; WO 97/32985; WO 97/42328; Takaha et al., 1993, J. Biol. Chem. 268: 1391–1396 or else in the EMBL database entry X83969, and those for ADP glucose pyrophosphorylases and plastid starch phosphorylase isoforms, for example, described in EP-A-0368506; EP-A-0455316; WO 94/28146; DE 19653176.4; WO 97/11188; Brisson et al., 1989, The Plant Cell 1:559–566; Buchner et al., 1996, Planta 199:64–73; Camirand et al., 1989, Plant Physiol. 89(4 Suppl.) 61; Bhatt & Knowler, J. Exp. Botany 41 (Suppl.) 5–7; Lin et al., 1991, Plant Physiol. 95: 1250–1253; Sonnewald et al., 1995, Plant Mol. Biol. 27:567–576; DDBJ No. D23280; Lorberth et al., 1998, Nature Biotechnology 16:473–477.

The nucleotide sequences to be employed suitably in accordance with the invention are of pro- or eukaryotic origin, preferably of bacterial, fungal or plant origin.

The term "parts of nucleotide sequences" denotes, for the purposes of the present invention, parts of the nucleotide sequences to be used in accordance with the invention which are at least 15 bp, preferably at least 150 bp, especially preferably at least 500 bp in length, but which do not exceed a length of 5000 bp, preferably 2500 bp.

The term "hybridization" means, for the purposes of the present invention, hybridization under conventional hybridization conditions, preferably under stringent conditions, as are described, for example, in Sambrook et al., Molecular Cloning, A Laboratory Manual, 2nd Ed. (1989) Cold Spring Harbor Laboratory Press, Cold Spring Harbor, N.Y.).

A "specific hybridization" especially preferably takes place under the following highly stringent conditions:

Hybridization buffer: 2×SSC; 10×Denhardt solution (Fikoll 400+PEG+BSA; ratio 1:1:1); 0.1% SDS; 5 mM EDTA; 50 mM $Na_2HPO_4$; 250 µg/ml herring sperm DNA; 50 µg/ml tRNA; or 0.25 M sodium phosphate buffer pH 7.2; 1 mM EDTA; 7% SDS at a

| | |
|---|---|
| Hybridization temperature: | T = 55 to 68° C., |
| Wash buffer: | 0.2 × SSC; 0.1% SDS and |
| Wash temperature: | T = 40 to 68° C., |

The molecules which hybridize with the nucleic acid molecules according to the invention also encompass fragments, derivatives and allelic variants of the nucleic acid molecules according to the invention. Fragments are to be understood as meaning parts of the nucleic acid molecules which are long enough to encode a functionally active part of the proteins described. The term derivative means in this context that the sequences of these molecules differ from the sequences of the nucleic acid molecules according to the invention in one or more positions and exhibit a high degree of homology to these sequences. Homology means a sequence identity of at least 60%, preferably over 70% and especially preferably over 85%. The deviations relative to the nucleic acid molecules according to the invention may have originated by means of deletions, substitutions, insertions or recombinations.

Homology furthermore means that functional and/or structural equivalence exists between the nucleic acid molecules in question or the proteins encoded by them. The nucleic acid molecules which are homologous to the molecules according to the invention and which constitute derivatives of these molecules are, as a rule, variations of these molecules which constitute modifications which exert the same biological function. They may be naturally occurring variations, for example sequences from other plant species, or mutations, it being possible for these mutations to have occurred naturally or to have been introduced by directed mutagenesis. The variations may further be synthetic sequences. The allelic variants may be naturally occurring variants or else synthetic variants or variants generated by recombinant DNA technology.

The nucleic acid molecules according to the invention may be DNA molecules, in particular cDNA or genomic molecules. The nucleic acid molecules according to the invention may furthermore be RNA molecules. The nucleic acid molecules according to the invention or parts thereof can have been obtained, for example, from natural sources or generated by means of recombinant technology or by synthesis.

To express the nucleic acid molecules according to the invention in sense or antisense orientation in plant cells, they are linked to regulatory DNA elements which ensure transcription in plant cells. These include, in particular, promoters. In general, any promoter which is active in plant cells is suitable for expression. The promoter may have been chosen in such a way that expression is constitutive or only in a particular tissue, at a particular point in time of plant development or at a point in time determined by external factors which can be, for example, chemically or biologically inducible. Relative to the transformed plant, the promoter—and also the nucleotide sequence—can be homologous or heterologous. Examples of suitable promoters are the cauliflower mosaic virus 35S RNA promoter for constitutive expression, the patatin gene promoter B33 (Rocha-Sosa et al., 1989, EMBO J. 8:23–29) for tuber-specific expression in potatoes or a promoter which ensures expression only in photosynthetically active tissues, for example the ST-LS1 promoter (Stockhaus et al., 1987, Proc. Natl. Acad. Sci. USA 84: 7943–7947; Stockhaus et al., 1989, EMBO J. 8: 2445–2451) or, for endosperm-specific expression, the wheat HMG promoter or promoters from maize zein genes.

A termination sequence which terminates the nucleic acid molecule according to the invention may serve to correctly end transcription and to add to the transcript a poly-A tail, which is considered to have a function in stabilizing the transcripts. Such elements have been described in the literature (cf. Gielen et al., 1989, EMBO J. 8:23–29) and are exchangeable as desired.

The nucleic acid molecules according to the invention can be used for generating transgenic plant cells and plants which show an increase or reduction in the activity of β-amylase or in the activity of β-amylase and at least one further enzyme of starch metabolism. To this end, the nucleic acid molecules according to the invention are introduced into suitable vectors, provided with the regulatory nucleic acid sequences which are necessary for efficient transcription in plant cells, and introduced into plant cells. On the one hand, there is the possibility of using the nucleic acid molecules according to the invention for inhibiting the synthesis of the endogenous β-amylase or the endogenous β-amylase and at least one further protein of group A in the cells. This can be achieved with the aid of antisense constructs, in-vivo mutagenesis, a cosuppression effect which occurs, or with the aid of suitably constructed ribozymes. On the other hand, the nucleic acid molecules according to the invention can be used for expressing β-amylase or β-amylase and at least one further protein of group A in the cells of transgenic plants and thus lead to an increased activity in the cells of the enzymes which have been expressed in each case.

In addition, there exists the possibility of using the nucleic acid molecules according to the invention for inhibiting the synthesis of the endogenous β-amylase and the overexpression of at least one further protein of group A in the cells.

Finally, the nucleic acid molecules according to the invention can also be used for expressing β-amylase and inhibiting at least one further protein of group A in the cells of transgenic plants. The two last-mentioned embodiments of the invention thus lead, in the cells, to a simultaneous inhibition and increase in the activities of the enzymes which are inhibited or expressed, respectively.

The invention furthermore relates to a vector comprising a nucleic acid molecule according to the invention.

The term "vector" encompasses plasmids, cosmids, viruses, bacterio-phages and other vectors conventionally used in genetic engineering which contain the nucleic acid molecules according to the invention and which are suitable for transforming cells. Such vectors are preferably suitable for transforming plant cells. Especially preferably, they permit integration of the nucleic acid molecules according to the invention, if appropriate together with flanking regulatory regions, into the genome of the plant cell. Examples are binary vectors, such as pBinAR or pBinB33, which can be employed in agrobacteria-mediated gene transfer.

In a preferred embodiment, the vector according to the invention is distinguished by the fact that the nucleotide sequence encoding a protein with the function of a β-amylase or parts thereof is present in sense or antisense orientation.

In a further preferred embodiment, the vector according to the invention is distinguished by the fact that the nucleotide sequence which encodes one or more proteins selected from amongst group A or parts thereof is present in sense or antisense orientation.

In yet a further preferred embodiment, the vector according to the invention is distinguished by the fact that the nucleotide sequence which encodes a plurality of proteins selected from group A or parts thereof is present partly in sense and partly in antisense orientation.

Very especially preferably, the vector according to the invention is linked to regulatory elements which ensure expression in a prokaryotic or eukaryotic cell, i.e., for example, transcription and synthesis of an RNA which, if the nucleotide sequence is present in sense orientation, is translatable.

In addition, it is possible to introduce, by means of customary techniques of molecular biology (see, for example, Sambrook et al., 1989, Molecular Cloning, A Laboratory Manual, 2nd Ed. Cold Spring Harbor Laboratory Press, Cold Spring Harbour, N.Y.), various mutations into the DNA sequences according to the invention, which leads to the synthesis of proteins with biological properties which may have been modified. On the one hand, it is possible to generate deletion mutants in which sequences are generated, by progressive deletions from the 5' or the 3' end of the coding DNA sequences which lead to the synthesis of analogously truncated proteins. For example, such deletions at the 5' end of the DNA sequence allow the targeted production of enzymes which, due to the removal of the relevant transit or signal sequences, are no longer localized in their original (homologous) compartment, but in the cytosol, or which, due to the addition of other signal sequences, are localized in one or more other (heterologous) compartments.

On the other hand, it is also feasible to introduce point mutations in positions where an altered amino acid sequence affects, for example, the enzyme activity or the regulation of the enzyme. Thus, it is possible, for example, to generate mutants which have an altered $K_M$ or $k_{cat}$ value or which are no longer subject to the regulatory mechanisms normally present in the cell via allosteric regulation or covalent modification.

For the purposes of recombination manipulation in prokaryotic cells, the DNA sequences according to the invention or parts of these sequences can be introduced into plasmids which permit mutagenesis or an altered sequence by the recombination of DNA sequences. Base exchanges may be performed or natural or synthetic sequences may be added, with the aid of standard methods in molecular biology (cf. Sambrook et al., 1989, loc. cit.). To link the DNA fragments to each other, adapters or linkers may be attached to the fragments. Furthermore, manipulations which provide suitable restriction cleavage sites or which remove excessive DNA or restriction cleavage sites which are no longer needed may be employed. Where insertions, deletions or substitutions are suitable, in-vitro mutagenesis, primer repair, restriction or ligation may be used. The analytical methods which are generally employed are sequence analysis, restriction analysis and, if appropriate, other methods of biochemistry and molecular biology.

The invention furthermore relates to a host cell, in particular prokaryotic or eukaryotic cells, preferably bacterial or plant cells (for example from E. coli, Agrobacterium, Solananceae, Poideae, rye, barley, oats, maize, wheat, sorghum and millet, sago, rice, peas, marrowfat peas, cassava, potatoes, tomatoes, oilseed rape, soybeans, hemp, flax, sunflowers, cowpeas, mung beans, beans, bananas or arrowroot) which contains a nucleic acid molecule according to the invention or a vector according to the invention or which is derived from a cell which has been transformed with a nucleic acid molecule according to the invention or a vector according to the invention.

The invention furthermore relates to a host cell, in particular prokaryotic or eukaryotic cells, preferably bacterial or plant cells (for example of E. coli, Agrobacterium, Solanaceae, Poideae, rye, barley, oats, maize, wheat, sorghum and millet, sago, rice, peas, marrowfat peas, cassava, potatoes, tomatoes, oilseed rape, soybeans, hemp, flax, sunflowers, cowpeas, mung beans, beans, bananas or arrowroot) which contains, in addition to a recombinant nucleic acid molecule encoding a protein with the function of a β-amylase, one or more further recombinant nucleic acid molecules which encode a protein selected from group A or their parts or nucleotide sequences hybridizing with these nucleic acid molecules.

In addition to using the nucleic acid molecules according to the invention, the host cells' according to the invention may, if appropriate, also be generated by successive transformation (so-called supertransformation), by employing individual nucleotide sequences or vectors comprising nucleotide sequences which encode a protein with the function of branching enzymes, ADP glucose pyrophosphorylases, granule-bound starch synthases, soluble starch synthases I, II, III or IV, debranching enzymes, disproportioning enzymes, plastid starch phosphorylases, R1 enzymes, amylases, glucosidases, parts thereof, and nucleic acid molecules which hybridizes with one of said nucleotide sequences or their parts, in a plurality of successive cell transformations.

A further embodiment of the present invention relates to a method of generating a transgenic plant cell which synthesizes a modified starch, which comprises integrating a nucleic acid molecule according to the invention or a vector according to the invention into the genome of a plant cell.

Providing the nucleic acid molecules according to the invention makes it possible to engage in the start metabolism of plants, with the aid of recombinant methods, and to alter it in such a way that the result is the synthesis of a modified starch which is altered relative to the starch synthesized in the wild-type plant with regard to, for example, structure, water content, protein content, lipid content, fiber content, ash/phosphate content, amylase/amylopectin ratio, molecular mass distribution, degree of branching, granule size, granule shape and crystallization, or else in its physicochemical properties such as the viscoelasticity, the sorptive characteristics, gelatinization temperature, viscosity, thickening capacity, solubility, gel structure, transparency, thermal stability, shear stability, stability to acids, tendency to undergo retrogradation, gelling, freeze-thaw stability, complex formation, iodine binding, film formation, adhesion power, enzyme stability, digestibility or reactivity. There is also the possibility of increasing the yield in suitably genetically modified plants by increasing the activity of proteins which are involved in starch metabolism, for example by overexpressing suitable nucleic acid molecules, or by providing mutants which are no longer subject to the cell's regulatory mechanisms and/or which exhibit different temperature dependencies relating to their activity. A particularly pronounced increase in yield may be the result of increasing the activity of one or more proteins which are involved in the starch metabolism in specific cells of the starch-storing tissue of transformed plants such as, for example,in the tuber in the case of potatoes or in the endosperm of maize or wheat. The economic importance and the advantages of these possibilities of engaging in the starch metabolism are obvious.

When expressing the nucleic acid molecules according to the invention in plants it is possible, in principle, for the protein synthesized to be localized in any desired compartment of the plant cell. To achieve localization in a particular compartment (cytosol, vacuole, apoplast, plastids, mitochondria), the transit or signal sequence which ensures localization must, if necessary, be deleted (removed) and the remaining coding region must, if necessary, be linked to DNA sequences which ensure localization in the compartment in question. Such sequences are known (see, for example, Braun et al., EMBO J. 11 (1992), 3219–3227; Wolter et al., Proc. Natl. Acad. Sci. USA 85 (1988), 846–850; Sonnewald et al., Plant J. 1 (1991), 95–106).

The generation of plant cells with a reduced activity of a protein involved in the starch metabolism can be achieved, for example, by expressing a suitable antisense RNA, a sense RNA for achieving a cosuppression effect, in-vivo mutagenesis or by expressing a suitably constructed ribozyme which specifically cleaves transcripts which encode one of the proteins involved in starch metabolism, using a nucleic acid molecule according to the invention, preferably by expressing an antisense transcript.

To this end, it is possible to use, firstly, a DNA molecule which encompasses all of the sequence which encodes a protein involved in starch metabolism including any flanking sequences, as well as DNA molecules which only encompass parts of the coding sequence, these parts having a minimum length of 15 bp, preferably of at least 100–500 bp, and in particular over 500 bp. As a rule, DNA molecules are used which are shorter than 5000 bp, preferably shorter than 2500 bp.

It is also possible to use DNA sequences which exhibit a high degree of homology to the sequences of the DNA molecules according to the invention, but are not fully identical with them. The minimum homology should exceed approx. 65%. The use of sequences with a homology of 75% and in particular 80% is to be preferred.

The expression of ribozymes for reducing the activity of specific proteins in cells is known to the skilled worker and described, for example, in EP-B1 0321 201. The expression of ribozymes in plant cells were described, for example, in Feyter et al. (Mol. Gen. Genet. 250 (1996), 329–338).

Furthermore, the reduction of the proteins involved in the starch metabolism in the plant cells according to the invention can also be achieved by so-called "in-vivo mutagenesis", where an RNA-DNA hybrid oligonucleotide ("chimeroplast") is introduced into cells by cell transformation (Kipp P. B. et al., Poster Session at the "5th International Congress of Plant Molecular Biology, 21–27, Sep. 1997, Singapore; R. A. Dixon and C. J. Arntzen, Meeting report on "Metabolic Engineering in Transgenic Plants", Keystone Symposia, Copper Mountain, Colo., USA, TIBTECH 15 (1997), 441–447; international patent application WO 95/15972; Kren et al., Hepatology 25 (1997), 1462–1468; Cole-Strauss et al., Science 273 (1996), 1386–1389).

Part of the DNA component of the RNA-DNA oligonucleotide used for this purpose is homologous to a nucleic acid sequence of an endogenous protein, but exhibits a mutation in comparison with the nucleic acid sequence of the endogenous protein or comprises a heterologous region enclosed by the homologous regions.

Base pairing of the homologous regions of the RNA-DNA oligonucleotide and of the endogenous nucleic acid molecule followed by homologous recombination allows the mutation or heterologous region contained in the DNA component of the RNA-DNA oligonucleotide to be transferred into the genome of a plant cell. This leads to a reduced activity of the protein involved in the starch metabolism.

As an alternative, the enzyme activities which are involved in the starch metabolism can be reduced in the plant cells by a cosuppression effect. This method is known to the skilled worker and is described, for example, by Jorgensen (Trends Biotechnol. 8 (1990), 340–344). Niebel et al., (Curr. Top. Microbiol. Immunol. 197 (1995), 91–103), Flavell et al. (Curr. Top. Microbiol. Immunol. 197 (1995), 43–46), Palaqui and Vaucheret (Plant. Mol. Biol. 29 (1995), 149–159), Vaucheret et al., (Mol. Gen. Genet. 248 (1995), 311–317), de Borne et al. (Mol. Gen. Genet. 243 (1994), 613–621) and other sources.

To inhibit the synthesis, in the transformed plants, of a plurality of enzymes involved in starch biosynthesis, it is possible to use DNA molecules for transformation which simultaneously contain, in antisense orientation and under the control of a suitable promoter, a plurality of regions which encode the relevant enzymes. Each sequence may be under the control of its own promoter, or, alternatively, the sequences can be transcribed by a joint promoter as a fusion, so that synthesis of the proteins in question is inhibited to approximately the same or to a different extent. As regards the length of the individual coding regions which are used in such a construct, what has already been said above for the generation of antisense constructs also applies here. In principle, there is no upper limit for the number of antisense fragments transcribed starting from a promoter in such a DNA molecule. However, the resulting transcript should not, as a rule, exceed a length of 25 kb, preferably 15 kb.

The nucleic acid molecules according to the invention make it possible to transform plant cells and simultaneously to inhibit the synthesis of a plurality of enzymes.

Moreover, it is possible to introduce the nucleic acid molecules according to the invention into traditional mutants which are deficient or defective with regard to one or more starch biosynthesis genes (Shannon and Garwood, 1984, in Whistler, BeMiller and Paschall, Starch: Chemistry and Technology, Academic Press, London, 2nd Edition: 25–86). These defects can relate, for example, to the following proteins: granule-bound (GBSSI) and soluble starch synthases (SSS I, II, III and IV), branching enzymes (BE I, IIa and IIb), debranching enzymes (R-enzymes, isoamylases, pullulanases), disproportioning enzymes and plastid starch phosphorylases.

The present invention thus also relates to transgenic plant cells obtainable by a process according to the invention which have been transformed with a nucleic acid molecule or vector according to the invention, and to transgenic plant cells derived from cells transformed in this way. The cells according to the invention contain a nucleic acid molecule according to the invention, this preferably being linked to regulatory DNA elements which ensure transcription in plant cells, in particular to a promoter. The cells according to the invention can be distinguished from naturally occurring plant cells, inter alia, by the fact that they contain a nucleic acid molecule according to the invention which does not occur naturally in these cells, or by the fact that such a molecule exists integrated at a location in the cell's genome where it does not occur otherwise, i,e. in a different genomic environment. Furthermore, the transgenic plant cells according to the invention can be distinguished from naturally occurring plant cells by the fact that they contain at least one copy of a nucleic acid molecule according to the invention stably integrated into their genome, if appropriate in addition to copies of such a molecule which occur naturally in the cells. If the nucleic acid molecule(s) introduced into the cells is (are) additional copies to molecules which already occur naturally in the cells, then the plant cells according to the invention can be distinguished from in naturally occurring plant cells in particular by the fact that this (these) additional copy (copies) is (are) localized at sites of the genome at which it (they) do(es) not occur naturally. This can be checked, for example, with the aid of a Southern blot analysis.

Preferred plant cells according to the invention are those in which the enzyme activity of individual enzymes which are involved in starch metabolism is increased or reduced by at least 10%, especially preferably by at least 30%, and very especially preferably by at least 50%.

Moreover, the plant cells according to the invention can be distinguished from naturally occurring plant cells preferably by at least one of the following features: if the nucleic acid molecule according to the invention which has been introduced is heterologous relative to the plant cell, the transgenic plant cells exhibit transcripts of the nucleic acid molecules according to the invention which have been introduced. This can be detected by, for example, northern blot analysis. For example, the plant cells according to the invention contain one or more proteins encoded by a nucleic acid molecule according to the invention which has been introduced. This can be detected by, for example, immunological methods, in particular by western blot analysis.

If the nucleic acid molecule according to the invention which has been introduced is homologous relative to the plant cell, the cells according to the invention can be distinguished from naturally occurring cells, for example, on the basis of the additional expression of nucleic acid molecules according to the invention. For example, the transgenic plant cells contain more or fewer transcripts of the nucleic acid molecules according to the invention. This can be detected by, for example, northern blot analysis. "More" or "fewer" in this context means preferably at least 10% more or fewer, preferably at least 20% more or fewer and especially preferably at least 50% more or fewer transcripts than corresponding untransformed cells. Furthermore, the cells preferably exhibit a corresponding (At least 10%, 20% or 50%, respectively) increase or decrease in the content of protein according to the invention. The transgenic plant cells can be regenerated into intact plants by techniques known to the skilled worker.

The plants obtainable by regenerating the transgenic plant cells according to the invention, and processes for the generation of transgenic plants by regenerating intact plants from the plant cells according to the invention, are also subject matter of the present invention. Another subject matter of the invention are plants which contain the transgenic plant cells according to the invention. In principle, the transgenic plants can be plants of any species, i.e. not only monocotyledonous, but also dicotyledonous plants. The plants are preferably useful plants, i.e. plants which are grown by man for the purposes of nutrition or for technical, in particular industrial, purposes. They are preferably starch-storing plants such as, for example, cereal species (rye, barley, oats, maize, wheat, sorghum and millet, sago etc.), rice, peas, marrowfat peas, cassava, potatoes, tomatoes, oilseed rape, soybeans, hemp, flax, sunflowers, cowpeas, mung beans or arrowroot.

The invention also relates to propagation material of the plants according to the invention, for example fruits, seeds, tubers, root stocks, seedlings, cuttings, calli, protoplasts, cell cultures etc.

Altering the enzymatic activities of the enzymes involved in starch metabolism results in the synthesis, in the plants generated by the process according to the invention, of a starch with a modified structure.

A large number of cloning vectors are available for preparing the introduction of foreign genes into higher plants, vectors which contain a replication signal for *E. coli* and a marker gene for the selection of transformed bacterial cells. Examples of such vectors are pBR322, pUC series, M13mp series, pACYC184 and the like. The desired sequence can be introduced into the vector at a suitable restriction cleavage site. The resulting plasmid is used for transforming *E. coli* cells. Transformed *E. coli* cells are cultured in a suitable medium and then harvested and lysed. The plasmid is recovered. The analytical methods for characterizing the plasmid DNA obtained are generally restriction analyses, gel electrophoreses and other methods of biochemistry and molecular biology (Sambrook et al. loc. cit.). After each manipulation, the plasmid DNA can be cleaved and DNA fragments obtained linked to other DNA sequences. Each plasmid DNA sequence can be cloned into the same or other plasmids.

A large number of techniques are available for introducing DNA into a plant host cell. These techniques encompass the transformation of plant cells with T-DNA using *Agrobacterium tumefaciens* or *Agrobacterium rhizogenes* as the means for transformation, protoplast fusion by means of polyethylene glycol (PEG), injection, DNA electroporation, the introduction of DNA by means of the biolistic method, and other possibilities.

The injection and electroporation of DNA into plant cells requires no particular aspects of the plasmids or the DNA used per se. Simple plasmids such as, for example, pUC derivatives can be used. However, if intact plants are to be regenerated from such transformed cells, the presence of a selectable marker gene is required.

Depending on the method of introducing desired genes into the plant cell, further DNA sequences may be required. If, for example, the Ti or Ri plasmid is used for transforming the plant cell, at least the right border, but frequently the right and left border, of the Ti and Ri plasmid T-DNA must be linked to the genes to be introduced as flanking region. If agrobacteria are used for the transformation, the DNA to be introduced must be cloned into specific plasmids, either into an intermediate vector or into a binary vector. The intermediate vectors can be integrated into the agrobacterial Ti or Ri plasmid by homologous recombination owing to sequences which are homologous to sequences in the T-DNA, The former also contains the vir region required for T-DNA transfer. Intermediate vectors cannot replicate in agrobacteria. The intermediate vector can be transferred to *Agrobacterium tumefaciens* by means of a helper plasmid (conjugation). Binary vectors are capable of replication in *E. coli* and in agrobacteria. They contain a selection marker gene and a linker or polylinker which are framed by the left and right T-DNA border region. They can be transformed directly into the agrobacteria (Holsters et al. (1978) Mol. Gen. Genet. 163: 181–187). The agrobacterium which acts as the host cell should contain a plasmid carrying a vir region. The vir region is required for transferring the T-DNA into the plant cell. Additional T-DNA may be present The agrobacterium transformed in this way is used for transforming plant cells.

The use of T-DNA for transforming plant cells has been researched intensively and been described in EP 120516; Hoekema, in: The Binary Plant Vector System Offsetdrukkerij Kanters B. V. Alblasserdam (1985), Chapter V; Fraley et al., Crit. Rev. Plant. Sci., 4: 146 and An et al. (1985) EMBO J. 4: 277–287.

To transfer the DNA into the plant cell, plant explants can expediently be cocultured with *Agrobacterium tumefaciens* or *Agrobacterium rhizogenes*. Intact plants can then be regenerated from the infected plant material (for example leaf sections, stem segments, roots, but also protoplasts, or plant cells which have been grown in suspension culture) in a suitable medium which can contain antibiotics or biocides for selecting transformed cells. The resulting plants can then be examined for the presence of the DNA which has been introduced. Other possibilities of introducing foreign DNA using the biolistic method or by protoplast transformation are known (cf., for example, Willmitzer, L, 1993 Transgenic plants. In: Biotechnology, A Multi-Volume Comprehensive Treatise (H. J. Rehm, G, Reed, A, Pühler, P. Stadler, eds.), Vol. 2, 627–659, VCH Weinheim-New York-Basle-Cambridge).

While the transformation of dicotyledonous plants via Ti-plasmid vector systems with the aid of *Agrobacterium tumefaciens* is well established, more recent work suggests that even monocotyledonous plants are indeed accessible to transformation by means of agrobacterium-based vectors (Chan et al., Plant Mol. Biol. 22 (1993), 491–506; Hiei et al., Plant J. 6 (1994), 271–282).

Alternative systems for the transformation of monocotyledonous plants are the transformation by means of the biolistic approach, protoplast transformation, the electroporation of partially permeabilized cells, and the introduction of DNA by means of glass fibers.

Specifically, different methods have been described in the literature for the transformation of maize (cf., for example, WO 95/06128, EP 0 513 849; EP 0 465 875). EP 292 435 describes a method with the aid of which fertile plants can be obtained starting from a mucilage-free, friable, granular maize callus. In this context, Shillito et al. (Bio/Technology 7 (1989), 581) have observed that the capacity of regenerating fertile plants requires starting from callus suspension cultures from which a dividing protoplast culture with the capacity of regenerating plants can be made. Following an in-vitro culture period of 7 to 8 months, Shillito et al. obtained plants with viable progeny which, however, have abnormalities with regard to morphology and reproductivity. Prioli and Söndahl (Bio/Technology 7 (1989), 589) also describe the regeneration and obtaining of fertile maize plants from maize protoplasts.

Once the DNA which has been introduced is integrated into the genome of the plant cell, it is, as a rule, stable therein and is also retained in the progeny of the originally transformed cell. It normally contains a selection marker which imparts to the transformed plant cells resistance to a biocide or an antibiotic such as kanamycin, G 418, bleomycin, hygromycin or phosphinotricin and the like. The individual marker chosen should therefore allow selection of transformed cells over cells which lack the DNA which has been introduced.

Within the plant, the transformed cells grow in the customary manner (see also McCormick et al. (1986) Plant Cell Reports 5:81–84). The resulting plants can be grown normally and hybridized with plants which have the same transformed germ plasm or other germ plasm. The resulting hybrids have the corresponding phenotypic features.

Two or more generations should be grown to ensure that the phenotypic feature is stably retained and inherited. Also, seeds should be harvested to ensure that the phenotype in question or other features have been retained.

Yet another subject matter of the invention is a process for the production of starch in a manner known per se, in which plant cells according to the invention, plants according to the invention, plant parts according to the invention or propagation material according to the invention are processed or integrated into the process.

Processes for extracting starch from plants or from starch-storing parts of plants are known to the skilled worker. Processes for extracting starch from maize kernels are described, for example, by Eckhoff et al. (Cereal Chem. 73 (1996) 54–57). As a rule, the extraction of maize starch on the industrial scale is performed by wet milling. Moreover, processes for extracting the starch from various starch-storing plants are described, for example, in "Starch: Chemistry and Technology (eds: Whistler, BeMiller and Paschall (1994), 2nd Edition, Academic Press Inc. London Ltd; ISBN 0-12-746270-8; see, for example, Chapter XII, pages 412–468: maize and sorghum starches: production; by Watson; Chapter XIII, pages 469–479: tapioca, arrowroot and sago starches: production; by Corbishley and Miller, Chapter XIV, pages 479–490: potato starch: production and uses; by Mitch; Chapter XV, pages 491 to 506: wheat starch: production, modification and uses; by Knight and Oson; and Chapter XVI, pages 507 to 528: rice starch: production and uses; by Rohmer and Klem). Devices normally used in processes for extracting starch from plant material are separators, decanters, hydrocyclones, spray dryers and fluidized-bed dryers.

Owing to the expression of a nucleic acid molecule according to the invention, the transgenic plant cells and plants according to the invention synthesize a starch which is modified in comparison to the starch synthesized in wild-type plants for example with regard to its physico-chemical properties.

Yet another subject matter of the invention is the starch which can be obtained from a plant cell according to the invention, plant according to the invention, their propagation material or a method according to the invention.

A further embodiment of the present invention also includes the use of the starch according to the invention in industry for the production of foodstuffs, packaging materials or disposable products.

The starch according to the invention can be modified by processes known to the skilled worker and is suitable, in its unmodified or modified form, for a variety of applications in the food or non-food sector.

In principle, the possible uses of the starch according to the invention can be divided into two important sectors. One sector encompasses the hydrolisates of the starch, mainly glucose and glucose units, which are obtained by enzymatic or chemical methods. They are used as starting material for other chemical modifications and processes such as fermentation. What may be important here is the simplicity and inexpensive design of a hydrolytic process as is currently performed essentially enzymatically using amyloglucosidase. What would be feasible is a financial saving by using less enzyme. This could be caused by altering the structure of the starch, for example increasing the surface area of the granule, by better degradability owing to a lower degree of branching, or by a steric structure which limits the accessibility for the enzymes employed.

The other sector in which starch according to the invention can be used as so-called native starch, due to its polymeric structure, can be divided into two further fields of application:

1. The Food Industry

Starch is a traditional additive to a large number of foodstuffs in which its function is essentially to bind aqueous additives or to cause increased viscosity or else increased gelling. Important characteristics are the viscoelasticity, the sorptive characteristics, the swelling temperature, the gelatinization temperature, the viscosity and thickening power, starch solubility, transparency and gel structure, thermal stability, shear stability, stability to acids, the tendency to undergo retrogradation, the film-forming capacity, the freeze-thaw stability, digestibility and the ability of forming complexes with, for example, inorganic or organic ions.

2. The Non-food Industry

In this important sector, starch is employed as an auxiliary for various preparation processes or as an additive in industrial products. When using starch as an auxiliary, mention must be made, in particular, of the paper and board industry. Starch acts mainly for retardation purposes (retaining solids), binding filler particles and fines, as a stiffener and for dehydration. Moreover, the advantageous properties of starch regarding stiffness, strength, sound, touch, luster, smoothness, bonding strength and the surfaces are made use of.

2.1. The paper and board industry

Within the papermaking process, four fields of application must be distinguished, i.e. surface, coating, stock and spraying. With 80% of the consumption, surface starch accounts for by far the greatest starch quantity, 8% are used as coating starch, 7% as stock starch and 5% as spraying starch.

The demands on starch with regard to surface treatment are essentially high whiteness, an adapted viscosity, highly stable viscosity, good film formation and low dust formation. When used for coating, the solids content, an adapted viscosity, a high binding capacity and a high pigment affinity play an important role. Of importance when used as an additive to the stock is rapid, uniform, loss-free distribution, high mechanical strength and complete retention in the paper web. If the starch is used in the spraying sector, again, an adapted solids content, high viscosity and a high binding capacity are of importance.

2.2. The adhesives industry

An important field of application for starches is in the adhesives industry, where the potential uses can be divided into four subsections: the use as a pure starch paste, the use in starch pastes which have been treated with specialty chemicals, the use of starch as additive to synthetic resins and polymer dispersions, and the use of starches as extenders for synthetic adhesives. 90% of the starch based adhesives is employed in the sectors production of corrugated board, production of paper sacks and bags, production of composite materials for paper and aluminum, production of box board and gumming adhesives for envelopes, stamps and the like.

2.3. The textiles and textile care products industry

An important field of application for starches as auxiliaries and additive is the sector production of textiles and textile care products. The following four fields of application must be distinguished within the textiles industry: the use of starch as sizing agent, i.e. as auxiliary for smoothing and strengthening the burring behavior as a protection from the tensile forces applied during weaving, and for increasing resistance to abrasion during weaving, starch as a textile finishing agent, in particular after quality-reducing pretreatments such as bleaching, dyeing and the like, starch as thickener in the preparation of dye pastes for preventing bleeding, and starch as additive to chaining agents for sewing threads.

2.4. The construction materials industry

The fourth field of application is the use of starches as additive in construction materials. An example is the production of gypsum plasterboards, where the starch which is admixed to the gypsum slurry gelatinizes with the water, diffuses to the surface of the plaster core, where it binds the boards to the core. Other fields of application are the admixture to rendering and mineral fibers. In the case of ready-mixed concrete, starch products are employed for delaying binding.

2.5. Soil stabilization

A limited market for starch products is the production of soil stabilizers, which are employed for the temporary protection of the soil particles from water when the soil is disturbed artificially. According to present knowledge, product combinations of starch and polymer emulsions equal the previously employed products with regard to their erosion- and crust-reducing effect, but are markedly less expensive.

2.6. Use in crop protection products and fertilizers

One field of application for using starch is in crop protection products for altering the specific properties of the products. Thus, starches are employed for improving the wettability of crop protection products and fertilizers, for the controlled release of the active ingredients, for converting liquid active ingredients, volatile active ingredients and/or active ingredients with an offensive odor into microcrystalline, stable, shapeable substances, for mixing incompatible compounds, and for extending the duration of action by reducing decomposition.

2.7. Pharmaceuticals, medicine, and the cosmetics industry

Another field of application is the sector of pharmaceuticals, medicine and the cosmetics industry. In the pharmaceuticals industry, starches are employed as binders for tablets or for diluting the binder in capsules. Moreover, starches are used as tablet disintegrants, since they absorb fluids after swallowing and swell within a short time to such an extent that the active ingredient is liberated. Medicinal lubricating powders and wound powders are starch-based for reasons of quality. In the cosmetics sector, starches are employed, for example, as carriers of powder additives such as fragrances and salicylic acid. A relatively large field of application for starch is toothpaste.

2.8. Addition of starch to coal and briquettes

A field of application for starch is as additive to coal and briquettes. With an addition of starch, coal can be agglomerated, or briquetted, in terms of high quantity, thus preventing early decomposition of the briquettes. In the case of barbecue coal, the starch addition amounts to between 4 and 6%, in the case of calorized coal to between 0.1 and 0.5%. Moreover, starches are gaining importance as binders since the emission of noxious substances can be markedly reduced when starches are added to coal and briquettes.

2.9. Ore slick and coal silt processing

Furthermore, starch can be employed as flocculant in ore slick and coal silt processing.

2.10. Foundry auxiliary

A further field of application is as additive to foundry auxiliaries. Various casting processes require cores made with sands treated with binders. The binder which is predominantly employed nowadays is bentonite, which is treated with modified starches, in most cases swellable starches.

The purpose of adding starch is to increase flowability and to improve the binding power. In addition, the swellable starches can meet the demands of production engineering, such as being cold-water dispersible, rehydratable and readily miscible with sand and having high water binding capacity.

2.11. Use in the rubber industry

In the rubber industry, starch is employed for improving the technical and visual quality. The reasons are the improvement of the surface luster, the improvement of handle and of appearance, and to this end starch is scattered over the tacky gummed surfaces of rubber materials prior to cold curing, and also the improvement of the rubber's printability.

2.12. Production of leather substitutes

Modified starches may furthermore also be sold for the production of leather substitutes.

2.13. Starch in synthetic polymers

In the polymer sector, the following fields of application can be envisaged: the incorporation of starch degradation products in the processing process (starch is only a filler, there is no direct bond between the synthetic polymer and the starch) or, alternatively, the incorporation of starch degradation products in the production of polymers (starch and polymer form a stable bond).

The use of starch as pure filler is not competitive in comparison with other substances such as talc. However, this is different when the specific properties of starch make an impact and thus markedly alter the spectrum of characteristics of the end products. An example of this is the use of starch products in the processing of thermoplasts, such as polyethylene. Here, the starch and the synthetic polymer are combined by coexpression in the ratio 1:1 to give a master batch, from which various products are produced together with granulated polyethylene, using conventional process techniques. By incorporating starch in polyethylene films, an increased substance permeability in the case of hollow bodies, an improved permeability for water vapor, an improved antistatic behavior, an improved antiblock behavior and an improved printability with aqueous inks can be achieved. The current disadvantages relate to the insufficient transparency, the reduced tensile strength, and a reduced elasticity.

Another possibility is the use of starch in polyurethane foams. By adapting the starch derivatives and by processing-engineering optimization, it is possible to control the reaction between synthetic polymers and the starches' hydroxyl groups in a direct manner. This results in polyurethane films which have the following spectrum of properties, owing to the use of starch: a reduced heat extension coefficient, a reduced shrinking behavior, an improved pressure-tension behavior, an increase in permeability for water vapor without altering the uptake of water, a reduced flammability and a reduced ultimate tensile strength, no drop formation of combustible parts, freedom from halogens, and reduced aging. Disadvantages which still exist are a reduced printability and a reduced impact strength.

Product development is currently no longer restricted to films. Solid polymer products such as pots, slabs and dishes with a starch content of over 50% may also be produced. Moreover, starch/polymer mixtures are considered advantageous since their biodegradability is much higher.

Starch graft polymers have become exceedingly important owing to their extremely high water binding capacity. They are products with a starch backbone and a side chain of a synthetic monomer, grafted on using the principle of the free-radical chain mechanism. The starch graft polymers which are currently available are distinguished by a better binding and retention capacity of up to 1000 g water per g of starch, combined with high viscosity. The fields of application for these superabsorbers have extended greatly in recent years and are, in the hygiene sector, the products diapers and pads, and, in the agricultural sector, for example in seed coatings.

What is decisive for the application of novel, genetically modified starches are, on the one hand, structure, water content, protein content, lipid content, fiber content, ash/phosphate content, amylose/amylopectin ratio, molecular mass distribution, the degree of branching, granule size, granule shape and crystallization, and, on the other hand, also the characteristics which affect the following features: viscoelasticity, sorption characteristics, gelatinization temperature, viscosity, thickening powder, solubility, gel structure, transparency, thermal stability, shear stability, stability to acids, tendency to undergo retrogradation, gel formation, freeze-thaw stability, complex formation, iodine binding, film formation, adhesive power, enzyme stability, digestibility and reactivity.

The production of modified starches by recombinant methods can, on the one hand, alter the properties, for example of the starch derived from the plant, in such a way that other modifications by means of chemical or physical alterations are no longer required. On the other hand, starches which have been modified by recombinant methods may be subjected to further chemical modifications, which leads to further improvements in quality for some of the above-described fields of application. These chemical modifications are known in principle. They are, in particular, modifications by thermal and pressure treatment, treatment with organic or inorganic acids, enzymatic treatment, oxidations or esterifications which lead, for example, to the formation of phosphate starches, nitrate starches, sulfate starches, xanthate starches, acetate starches and citrate starches. Moreover, mono- or polyhydric alcohols in the presence of strong acids may be employed for producing starch ethers, resulting in starch alkylethers, O-allyl ethers, hydroxyalkyl ethers, O-carboxylmethyl ethers, N-containing starch ethers, P-containing starch ethers, S-containing starch ethers, crosslinked starches or starch graft polymers.

A use of the starches according to the invention is in industrial application, preferably for foodstuffs or the production of packaging materials and dispersible articles.

The examples which follow serve to illustrate the invention and constitute in no way a restriction.

| Abbreviations used: | |
|---|---|
| BE | branching enzyme |
| bp | base pair |
| IPTG | isopropyl β-D-thiogalactopyranoside |
| SS | soluble starch synthase |
| PMSF | phenylmethylsulfonyl fluoride |
| Media and solution used in the examples: | |
| 20 × SSC | 175.3 g NaCl |
| | 88.2 g sodium citrate |
| | to 1000 ml with twice-distilled H$_2$O |
| | pH 7.0 with 10 N NaOH |
| Buffer A | 50 mM Tris-HCl pH 8.0 |
| | 2.5 mM DTT |
| | 2 mM EDTA |
| | 0.4 mM PMSF |
| | 10% glycerol |
| | 0.1% sodium dithionite |
| Buffer B | 50 mM Tris-HCl pH 7.6 |
| | 2.5 mM DTT |
| | 2 mM EDTA |
| Buffer C | 0.5 M sodium citrate pH 7.6 |
| | 50 mM Tris-HCl pH 7.6 |
| | 2.5 mM DTT |
| | 2 mM EDTA |
| 10 × TBS | 0.2 M Tris-HCl pH 7.5 |
| | 5.0 M NaCl |
| 10 × TBST | 10 × TBS |
| | 0.1% (v/v) Tween 20 |
| Elution buffer | 25 mM Tris pH 8.3 |
| | 250 mM glycine |
| Dialysis buffer | 50 mM Tris-HCl pH 7.0 |
| | 50 mM NaCl |
| | 2 mM EDTA |
| | 14.7 mM β-mercaptoethanol |
| | 0.5 mM PMSF |
| Protein buffer | 50 mM sodium phosphate buffer pH 7.2 |
| | 10 mM EDTA |
| | 0.5 mM PMSF |
| | 14.7 mM β-mercaptoethanol |

DESCRIPTION OF THE FIGURES

FIG. 1 represents a schematic RVA temperature profile (viscosity vs. time [min]) with the viscosimetric parameters T=gelatinization temperature, temperature at the point in time when gelatinization starts; Max specifies the maximum viscosity; Min specifies the minimum viscosity; Fin specifies the viscosity at the end of the measurement; Set is the difference (Δ) of Min and Fin (setback).

THE FOLLOWING METHODS WERE USED IN THE EXAMPLES

1. Cloning Method

The vector pBluescript II SK (Stratagene) was used for cloning into *E. coli*.

For the transformation of plants, the gene constructions were cloned into the binary vector pBinAR Hyg (Höfgen & Willmitzer, 1990, Plant Sci. 66:221–230) and pBinB33-Hyg.

2. Bacterial Strains and Plasmids

The *E. coli* strain DH5α (Bethesda Research Laboratories, Gaithersburgh, USA) was used for the Bluescript vector p Bluescript II KS (Stratagene) and for the pBinAR Hyg and pBinB33 Hyg constructs. The *E. coli* strain XL1-Blue was used for the in vivo exclusion.

pBinAR

The plasmid pBinAR is a derivative of the binary vector plasmid pBin19 (Bevan, 1984, Nucl. Acid Res. 12:8711–8721), which was constructed as follows: a 529 bp fragment encompassing the nucleotides 6909–7437 of the cauliflower mosaic virus promoter 35S promoter was isolated from plasmid pDH51 as EcoRI/KpnI fragment (Pietrzak et al., 1986), ligated between the EcoRI and KpnI cleavage sites of the pUC18 polylinker, and was termed plasmid pUC18-35S. With the aid of the restriction endonucleases HindIII and PvuII, a 192 bp fragment was isolated from plasmid pAGV40 (Herrera-Estrella et al., 1983), which encompasses DNA of the Ti-plasmid pTiACH5 (Gielen et al, 1984, EMBO J.:835–846) (nucleotides 11749–11939). After the PvuII cleavage sites had been provided with SphI linkers, the fragment was ligated between the SpHI and HindIII cleavage sites of pUC18-35S, and this was termed plasmid pA7. Moreover, the entire polylinker comprising the 35S promoter and the ocs terminator was excised with EcoRI and HindIII and ligated into the appropriately cleaved pBin19. This gave rise to the plant expression vector pBinAR (Höfgen and Willmitzer, 1990).

pBinB33

The promoter of the *Solanum tuberosum* patatin gene B33 (Rocha-Sosa et al., 1989) was ligated, as DraI fragment (nucleotides −1512−+14) into the vector pUC19, which had been cleaved with SstI and which had been made blunt-ended with the aid of T4-DNA polymerase. This gave rise to plasmid pUC19-B33. The B33 promoter was excised from this plasmid with EcoRI and SmaI and ligated into the appropriately cleaved vector pBinAR, This gave rise to the plant expression vector pBinB33.

pBinAR-Hyg

Starting from plasmid pA7 (cf. description of vector pBinAR), the EcoRI-HindIII fragment comprising the 35S promoter, the ocs terminator and the portion of the polylinker situated between the 35S promoter and the ocs terminator was introduced into the appropriately cleaved plasmid pBin-Hyg.

pBinB33-Hyg

Starting from plasmid pBinB33, the EcoRI-HindIII fragment comprising the B33 promoter, part of the polylinker and the ocs terminator was excised and ligated into the appropriate cleaved vector pBin-Hyg. This gave rise to the plant expression vector pBinB33-Hyg.

3. Transformation of *Agrobacterium Tumefaciens*

The DNA was transferred by direct transformation using the method of Höfgen&Willmitzer (1988, Nucleic Acids Res. 16:9877). The plasmid DNA of transformed agrobacteria was isolated using the method of Birnboim&Doly (1979, Nucleic Acids Res. 7:1513–1523), subjected to suitable restriction cleavage, and then analyzed by gel electrophoresis.

4. Transformation of Potatoes

The transformation of the plasmids into the potato plants (*Solanum tuberosum* L.cv. Desiree, Vereinigte Saatzuchten eG, Ebstorf) was carried out with the aid of the *Agrobacterium tumefaciens* strain C58C1 (Dietze et al. (1995) in Gene Transfer to Plants. pp. 24–29, eds.: Potrykus, I. and Spangenberg, G., Springer Verlag, Deblaere et al., 1985, Nucl. Acids Res. 13:4777–4788).

Ten small leaves of a sterile potato culture which had been scarified with a scalpel were placed into 10 ml of MS medium (Murashige&Skoog (1962) Physiol. Plant. 15: 473) supplemented with 2% sucrose and containing 50 ml of an *Agrobacterium tumefaciens* overnight culture grown under selection conditions. After the culture had been shaken gently for 3–5 minutes, it was incubated for 2 more days in the dark. For callus induction, the leaves were then placed on MS medium supplemented with 1.6% glucose, 5 mg/l naphthylacetic acid, 0.2 mg/l benzylaminopurin, 250 mg/l claforan, 50 mg/l kanamycin, and 0.80% Bacto agar. After the leaves had been incubated for one week at 25° C. and 3000 Lux, they were placed on MS medium supplemented with 1.6% glucose, 1.4 mg/l zeatin ribose, 20 mg/l naphthylacetic acid, 20 mg/l giberellic acid, 250 mg/l claforan, 50 mg/l kanamycin and 0.80% Bacto agar, to induce shoots.

5. Plant Culture Regime

Potato plants were kept in the greenhouse under the following conditions:

light period 16 h at 25,000 Lux and 22° C.
dark period 8 h at 15° C.
atmospheric humidity 60%

6. Radiolabeling of DNA Fragments

The DNA fragments were radiolabeled with the aid of a DNA Random Primer Labeling Kit by Boehringer Mannheim (Germany) following the manufacturer's instructions.

7. Determination of Starch Synthase Activity

Determination of starch synthase activity was done by determining the incorporation of $^{14}C$ glucose from ADP[$^{14}C$ glucose] into a product which is insoluble in methanol/KCl, as described by Denyer & Smith, 1992, Planta 186:609–617.

8. Detection of Soluble Starch Synthases in the Native Gel

To detect the activity of soluble starch synthases by non-denaturing gel electrophoresis, tissue samples of potato tubers were hydrolyzed in 50 mM Tris-HCl pH 7.6, 2 mM DTT, 2.5 mM EDTA, 10% glycerol and 0.4 mM PMSF, The electrophoresis was carried out in a MiniProtean II chamber (BioRAD). The monomer concentration of the gels, which had a thickness of 1.5 mm, was 7.5% (w/v), and 25 mM Tris-glycine pH 8.4 was used as gel buffer and running buffer. Identical amounts of protein extract were applied and separated for 2 hours at 10 mA per gel.

The activity gels were subsequently incubated in 50 mM Tricine-NaOH pH 8.5, 25 mM potassium acetate, 2 mM EDTA, 2 mM DTT, 1 mM ADP-glucose, 0.1% (w/v) amylopectin and 0.5 M sodium citrate. The glucans formed were stained with Lugol's solution.

9. Starch Analysis

The starch formed by the transgenic potato plants was characterized by the following methods:

a) Determination of the Amylose/amylopectin Ratio in Starch from Potato Plants

Starch was isolated from potato plants by standard methods, and the amylose:amylopectin ratio was determined by the method described by Hovenkamp-Hermelink et al. (Potato Research 31 (1988) 241–246).

b) Determination of the Phosphate Content

In potato starch, some glucose units may be phosphorylated on the carbon atoms of position C2, C3 and C6. To determine the degree of phosphorylation at position C6 of the glucose, 100 mg of starch were hydrolyzed for 4 hours at 95° C. in 1 ml of 0.7 M HCl (Nielsen et al. (1994) Plant Physiol. 105: 111–117). Following neutralization with 0.7 M KOH, 50 ml of the hydrolysate were subjected to a visual-enzymatic test to determine glucose-6-phosphate. The change in absorption of the test batch (100 mM imidazole/HCl; 10 mM $MgCl_2$; 0.4 mM NAD; 2 units Leuconostoc mesteroides glucose6-phosphate dehydrogenase; 30° C.) was monitored at 334 nm.

The total phosphate was determined as described by Ames, 1996, Methods in Enzymology VIII, 115–118.

c) Analysis of the Amylopectin Side Chains

To analyze distribution and length of the side chains in the starch samples, 1 ml of a 0.1% starch solution was digested with 0.4 U of isoamylase (Megazyme International Ireland Ltd., Bray, Ireland) overnight at 37° C. in 100 mM sodium citrate buffer, pH 3.5.

The rest of the analysis was carried out as described by von Tomlinson et al., (1997), Plant J. 11:31–47, unless otherwise specified.

d) Granule size determination

The granule size was determined using a "Lumosed" photosedimentometer by Retsch GmbH, Germany. To this end, 0.2 g of starch was suspended in approx. 150 ml of water and immediately measured. The program supplied by the manufacturer calculated the mean diameter of the starch granules, assuming an average starch density of 1.5 g/l.

e) Gelatinization properties

The gelatinization or viscosity properties of the starch were recorded using a Viscograph E by Brabender oHG, Germany, or a Rapid Visco Analyser, Newport Scientific Pty Ltd., Investment Support Group, Warriewood NSW 2102, Australia. When using the Viscograph E, a suspension of 30 g of starch in 450 ml of water was subjected to the following heating program: heat from 50° C. to 96° C. at 3°/min, hold for 30 minutes, cool to 30° C. at 3°/min and hold again for 30 minutes. The temperature profile gave characteristic gelatinization properties.

When measuring using the Rapid Visco Analysers (RVA) a suspension of 2 g of starch in 25 ml of water was subjected to the following heating program: suspend for 60 seconds at 50° C., heat from 50° C. to 95° C. at 12°/min, hold for 2.5 minutes, cool to 50° C. at 12° C./min and hold again for 2 minutes. The RVA temperature profile gave the viscosimetric parameters of the tested starches for the maximum viscosity (Max), the end viscosity (Fin), the gelatinization temperature (T), the minimum viscosity (Min) occurring after the maximum viscosity and the difference between minimum viscosity and end viscosity (Setback, Set) (cf. Table 1 and FIG. 1).

f) Determination of the Gel Strength

To determine the gel strength by means of a Texture Analyser, 2 g of starch were gelatinized in 25 ml of water (cf. RVA measurement) and then stored for 24 hours in a sealed container at 25° C. with the exclusion of air. The samples were mounted underneath the probe (circular stamp) of a TA-XT2 Texture Analyser (Stable Micro Systems), and the gel strength was determined with the following parameter settings:

| | |
|---|---|
| Test speed | 0.5 mm |
| Penetration depth | 7 mm |
| Contact area (of the stamp) | 113 mm$^2$ |
| Pressure/contact area | 2 g |

10. Determination of Glucose, Fructose and Sucrose

To determine the glucose, fructose and sucrose content, small tuber portions (diameter approx. 10 mm) of potato tubers were frozen in liquid nitrogen and then extracted for 30 minutes at 80° C. in 0.5 ml of 10 mM HEPES, pH 7.5; 80% (v/v) ethanol. The supernatant, which contains the solubles, was removed and the volume was determined. The supernatant was used for determining the amount of soluble sugars. The quantitative determination of soluble glucose, fructose and sucrose was carried out in a batch of the following composition

| | |
|---|---|
| 100.0 mm imidazole/HCl, pH 6.9 | |
| 1.5 mM MgCl$_2$ | |
| 0.5 mM NADP$^+$ | |
| 1.3 mM ATP | |
| 10–50 µl sample | |
| 1.0 U yeast glucose-6-phosphate dehydrogenase | |

The batch was incubated for 5 minutes at room temperature. The sugars were subsequently determined photometrically by measuring the absorption at 340 nm after the successive addition of 1.0 units yeast hexokinase (to determine glucose),
1.0 units yeast phosphoglucoisomerase (to determine fructose), and
1.0 units yeast invertase (to determine sucrose).

USE EXAMPLES

Example 1

Isolation of a cDNA Fragment Encoding Potato β-amylase

Approximately 6×10$^6$ plaque-forming units (pfUs) of a tumor-specific cDNA potato library (λ ZAPII, Stratagene) were excised in vivo according to the manufacturer's instructions (Stratagene) and some of the phagmid stock was used for the transfection of E.coli XL1-MRF cells (according to the manufacturer's instructions). Plasmid DNA was prepared from approximately 5×10$^5$ such E.coli transformants (Sambrook et al., 1989, loc. cit.) and used for transformation of cells of the E.coli strain by KV832/pACAG (Abel, G, 1995, PhD Thesis in the Faculty of Biology of the Technical University of Berlin) according to the electroporation method (BioRAD, according to the manufacturer's instructions).

The KV832/pACAG transformants were cultured at 37° C. with 1% glucose and 1 mM IPTG on YT medium (5 g/l of NaCl, 8 g/l of tryptone, 5 g/l of yeast extract). For selection for the presence of the plasmid pACAG, the medium contained 10 mg/l of chloramphenicol. For selection for positive transformants, the medium contained 100 mg/l of ampicillin.

After approximately 14 hours' growth, the colonies of the transformed cells were stained by means of iodine vapor. Plasmid DNA of markedly weakly colored colonies was prepared according to Bimboim & Doly (1979) and used for the transformation of E.coli DH5α (Sambrook et al., 1989, loc.cit.). Plasmid DNA of these transformants was employed for DNA sequencing and identified as SEQ ID NO: 1.

The plasmid selected in this way was deposited in the German Collection for Microorganisms in Brunswick, FRG, on 07.24.98 under the number DSM 12348 and contains an Asp 718/BamHI fragment about 1300 bp long of the nucleotide sequence shown as Seq ID No. 1 encoding a β-amylase from Solanum tuberosum between the CAMV 353 promoter and the ocs terminator.

Example 2

Preparation of Plasmid p35SαSSI-Hyg

A 1831 bp Asp718/XbaI fragment containing a partial cDNA encoding the potato SSSI (Abel, G, (1995) PhD Thesis, Free University of Berlin), was inserted between the Asp 718 and XbaI cleavage site of the vector pBinAR-Hyg in antisense orientation relative to the 35S promoter.

Example 3

Preparation of Plasmid p35S-SSI-Kan

A 2384 bp EcoRI fragment containing a cDNA encoding potato SSI (Abel 1995, loc. cit.) was made blunt-ended and introduced into the vector pBinAR, which had previously been cut with SmaI, in sense orientation relative to the 35S promoter.

Example 4

Preparation of Plasmid p35SαSSI-Kan

A 1959 bp SmaI/Asp718 fragment containing a partial cDNA encoding the potato SSII (Abel, 1995, termed GBSSII therein) was made blunt-ended and introduced into the SmaI cleavage site of the vector pBinAR in antisense orientation relative to the 35S promoter.

Example 5

Preparation of Plasmid pB33-SSII-Hyg

A 2619 bp SmaI/SalI fragment containing a cDNA encoding the potato SSII (Abel, 1995, loc. cit.) was introduced into the vector pBinB33-Hyg, which had previously been cut with SmaI and SalI in sense orientation relative to the B33 promoter.

Example 6

Preparation of Plasmid p35SαSSIII-Hyg

A 4212 bp Asp718/XbaI fragment containing a cDNA encoding the potato SSIII (Abel et al., 1996, Plant J. 10(6):981–991), was inserted between the Asp718 and the XbaI cleavage site of the vector pBinAR-Hyg in antisense orientation relative to the 35S promoter.

Example 7

Preparation of Plasmid p35S-SSIII-Kan

A 4191 bp EcoRI fragment containing a cDNA encoding potato SSIII (Abel et al., 1996, loc. cit.), was made blunt-ended and introduced into the SmaI cleavage site of the vector pBinAR in sense orientation relative to the 35S promoter.

Example 8

Preparation of Plasmid pB33αBEαSSIII-Kan

A 1650 bp HindII fragment which contains a partial cDNA encoding the potato BE enzyme (Kossmann et al., 1991, Mol. & Gen. Genetics 230(1–2):39–44) was made blunt-ended and introduced in antisense orientation relative to the B33 promoter into the vector pBinB33 which had been precut with SmaI. The resulting plasmid was cut open with BamHI. A 1362 Bp BamHI fragment containing a partial cDNA encoding the potato SSIII enzyme (Abel et al., 1996, loc. cit.) was introduced into the cleavage site, again in antisense orientation relative to the B33 promoter.

Example 9

Preparation of Plasmid p35SαSSII-αSSIII-Kan

A 1546 bp EcoRV/HincII fragment containing a partial cDNA encoding the potato SSII (Abel, 1995, loc. cit.) was cloned into the vector pBluescript II KS which can been cut with EcoRV/HincII, then excised again by digestion with Asp718/BamHI and introduced in antisense orientation relative to the 35S promoter into the vector pBinAR which had been digested in the same manner. Then, a 1356 bp BamHI fragment containing a partial cDNA encoding the potato SSIII (Abel et al., 1996, loc. cit.), was introduced into the BamHI cleavage site of the vector pBinAR-αSSII, again in antisense orientation.

Example 10

Preparation of Plasmid pB33αSSIαSSIαSSIII-Kan

A 2384 bp EcoRI fragment containing a cDNA encoding the potato SSI (Abel, 1995, loc. cit.) was made blunt-ended and cloned into the SmaI cleavage site of the pBinB33 vector in antisense orientation relative to the B33 promoter. A 1362 bp BamHI fragment containing a partial cDNA encoding the potato SSIII (Abel et al., 1996, loc. cit.) was introduced into the BamHI cleavage site of the resulting vector, again in antisense orientation relative to the B33 promoter.

Example 11

Preparation of Plasmid p35SαSSII-Hyg

A 1959 bp SmaI/Asp718 fragment containing a partial cDNA encoding the SSII (Abel, 1995, loc. cit.), was made blunt-ended and introduced into the SmaI cleavage site of the pBinAR-Hyg vector in antisense orientation relative to the 35S promoter.

Example 12

Introduction of the Plasmids Into the Genome of Potato Cells

The plasmids stated in Examples 1 to 11 were transferred, either individually and/or in succession, into agrobacteria, with the aid of which potato cells were transformed as described above. Subsequently, intact plants were regenerated from the transformed plant cells.

Example 13

Characterization of the Physico-chemical Properties of the Modified Starches

As a result of the transformation, the transgenic potato plants showed a change in the physico-chemical properties of the starches synthesized by them. The starch formed by these plants differs for example from starch synthesized in wild-type plants with regard to its phosphate or amylose content, the viscosity or gelatinization properties determined by RVA, and its chromatographic behavior.

I claim:

1. An isolated nucleic acid molecule encoding a protein with the function of a potato β-amylase, selected from the group consisting of:
   a) a nucleic acid molecule encoding the amino acid sequence of SEQ ID NO: 2;
   b) a nucleic acid molecule having the nucleotide sequence of SEQ ID NO: 1;
   c) a nucleic acid molecule which hybridizes with, or is complementary to, the nucleic acid molecules stated under a) or b), wherein hybridization is performed at a temperature of 68° C. in buffer comprising 2×SSC or 7% SDS and is followed by a wash at 68° C. in a wash buffer containing 0.2×SSC; and
   d) a nucleic acid molecule whose nucleotide sequence deviates from the sequence of the nucleic acid molecule stated under a)–c) owing to the degeneracy of the genetic code.

2. A recombinant nucleic acid molecule containing:
   a) the nucleic acid molecule encoding a protein with the function of a potato β-amylase as claimed in claim 1, and
   b) one or more nucleotide sequences which encode one or more proteins, wherein the one or more proteins are selected from the group consisting of branching enzymes, ADP glucose pyrophosphorylases, granule-bound starch synthases, soluble starch synthases, debranching enzymes, disproportioning enzymes, plastid starch phosphorylases, R1-enzymes, amylases, and glucosidases; or nucleic acid molecules which hybridize with said nucleotide sequences, wherein hybridization is performed at a temperature of 68° C. in buffer comprising 2×SSC or 7% SDS and is followed by a wash at 68° C. in a wash buffer containing 0.2×SSC.

3. The nucleic acid molecule as claimed in claim 1, which is a deoxyribonucleic acid molecule.

4. The nucleic acid molecule as claimed in claim 2, which is a cDNA molecule.

5. The nucleic acid molecule as claimed in claim 1, which is a ribonucleic acid molecule.

6. A vector comprising the nucleic acid molecule as claimed in claim 1.

7. A vector comprising the nucleic acid molecule as claimed in claim 1, wherein the nucleic acid molecule encoding a protein with the function of a β-amylase is present in sense orientation.

8. A vector comprising the recombinant nucleic acid molecule as claimed in claim 2, wherein the nucleic acid molecule encoding a β-amylase and the nucleotide sequence encoding one or more proteins of (b) are present in sense orientation.

9. A vector comprising the recombinant nucleic acid molecule as claimed in claim 2, further comprising nucleotide sequences which encode a plurality of proteins selected from the group consisting of branching enzymes, ADP glucose pyrophosphorylases, granule-bound starch synthases, soluble starch synthases, debranching enzymes, disproportioning enzymes, plastid starch phosphorylases, R1-enzymes, amylases, and glucosidases; or nucleic acid molecules which hybridize with said nucleotide sequences, wherein hybridization is performed at a temperature of 68° C. in buffer comprising 2×SSC or 7% SDS and is followed by a wash at 68° C. in a wash buffer containing 0.2×SSC, wherein at least one nucleotide sequence is in sense orientation and at least one nucleotide sequence is in antisense orientation.

10. A vector comprising at the nucleic acid molecule as claimed in claim 1, which nucleic acid molecule is operably linked to regulatory elements which ensure transcription and synthesis of an RNA, which is optionally translatable, in a pro- or eukaryotic cell.

11. A host cell which is transformed with the nucleic acid molecule as claimed in any one of claims 1–5, or with a vector as claimed in any one of claims 6–10, or a cell which is derived from the host cell and which contains said nucleic acid molecule or said vector.

12. A process for the generation of a transgenic plant cell which synthesizes a modified starch, comprising integrating the nucleic acid molecule as claimed in any one of claims 1–5 or a vector as claimed in any one of claims 6–10 into the genome of a plant cell.

13. A plant cell which is obtained by the process as claimed in claim 12.

14. A process for generating a transgenic plant which synthesizes a modified starch comprising regenerating an intact plant from the cell as claimed in claim 13.

15. A plant comprising the plant cell as claimed in claim 13.

16. The plant as claimed in claim 15, which is a starch-storing plant.

17. The plant as claimed in claim 15, which is a wheat, maize, potato or rice plant.

18. Propagation material of the plant as claimed in claim 15, wherein said propagation material comprises said nucleic acid molecule or said vector.

19. A process for the production of starch comprising isolating starch from the plant cells as claimed in claim 13, the plants as claimed in claim 15 or propagation material as claimed in claim 18.

20. The nucleic acid molecule of claim 2, wherein the one or more proteins are glucosidases.

* * * * *